United States Patent
Brümmer et al.

(10) Patent No.: US 6,965,004 B2
(45) Date of Patent: Nov. 15, 2005

(54) ETHYLENE-STYRENE COPOLYMERS AND PHENOL-TRIAZOLE TYPE COMPLEXES, CATALYSTS, AND PROCESSES FOR POLYMERIZING

(75) Inventors: Oliver Brümmer, Berlin (DE); Gary M. Diamond, San Jose, CA (US); Christopher Goh, San Francisco, CA (US); Anne M. LaPointe, Sunnyvale, CA (US); Margarete K. Leclerc, Santa Clara, CA (US); James Longmire, San Jose, CA (US); James A. W. Shoemaker, San Jose, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 0 days.

(21) Appl. No.: 10/850,585

(22) Filed: May 20, 2004

(65) Prior Publication Data

US 2004/0214717 A1 Oct. 28, 2004

Related U.S. Application Data

(62) Division of application No. 10/121,300, filed on Apr. 12, 2002, now Pat. No. 6,794,514.

(51) Int. Cl.$^7$ ............................ C08F 212/08; C08F 4/44
(52) U.S. Cl. ..................... 526/346; 526/347; 526/171; 502/155; 502/167; 548/146; 548/206
(58) Field of Search .................. 548/146, 206; 526/346, 347, 171; 502/155, 167

(56) References Cited

U.S. PATENT DOCUMENTS

| | | | |
|---|---|---|---|
| 3,004,896 A | 10/1961 | Heller et al. | |
| 3,390,141 A | 6/1968 | Richards | |
| 5,064,802 A | 11/1991 | Stevens et al. | 502/155 |
| 5,153,157 A | 10/1992 | Hlatky et al. | 502/117 |
| 5,180,872 A | 1/1993 | Starzewski | 585/435 |
| 5,453,410 A | 9/1995 | Kolthammer et al. | 502/155 |
| 5,599,761 A | 2/1997 | Turner | 502/152 |
| 5,616,664 A | 4/1997 | Timmers et al. | 526/127 |
| 5,919,983 A | 7/1999 | Rosen et al. | 568/3 |
| 6,175,409 B1 | 1/2001 | Nielsen et al. | 356/337 |
| 6,260,407 B1 | 7/2001 | Petro et al. | 73/61.52 |
| 6,265,226 B1 | 7/2001 | Petro et al. | 436/180 |
| 6,294,388 B1 | 9/2001 | Petro | 436/8 |
| 6,296,771 B1 | 10/2001 | Miroslav | 210/656 |
| 6,306,658 B1 | 10/2001 | Turner et al. | 436/37 |
| 6,706,829 B2 * | 3/2004 | Boussie et al. | 526/161 |
| 2001/0031843 A1 | 10/2001 | Whiteker et al. | 526/161 |

FOREIGN PATENT DOCUMENTS

| | | | |
|---|---|---|---|
| EP | 0 277 004 | 8/1988 | C08F/4/64 |
| EP | 0 526 943 | 10/1995 | C07C/2/34 |
| JP | 9-111234 | 4/1997 | |
| JP | 2000-25667 | 9/2000 | |
| JP | 2001-19681 | 1/2001 | |
| WO | WO 99/06413 | 2/1999 | C07F/5/02 |
| WO | WO 99/42467 | 8/1999 | C07F/5/02 |
| WO | WO 00/09255 | 2/2000 | B01J/19/00 |
| WO | WO 00/37512 | 6/2000 | C08F/10/00 |
| WO | WO 01/48035 | 7/2001 | C08F/10/00 |
| WO | WO 02/02577 | 1/2002 | C07F/17/00 |
| WO | WO 02/06358 | 1/2002 | C08F/10/00 |

OTHER PUBLICATIONS

Brintzinger et al., "Stereospecific Olefin Polymerization with Chiral Metallocene Catalysts", *Angew. Chem. Int. Ed. Engl.*, 1995, vol. 34, pp. 1143–1170.
Carlini et al., *Polymer*, 2001, 42, pp. 5069–5078.
Jordan, "Chemistry of Cationic Dicyclpentadienyl Group 4 Metal–Alkyl Complexes", *Adv. Organometallic Chem.*, 1991, vol. 32, pp. 325–387.
LaPointe et al., *J. Am. Chem. Soc.*, 2000, 122, 9560–9561.
Pellecchia et al., *Macromolecules*, 2000, 33, 2807–2814.
Piers et al., "New Bifunctional Perfluoroaryl Boranes: Synthesis and Reactivity of the *ortho*–Phenylene–Bridged Diboranes 1,2–[B(C$_6$F$_5$)$_2$]$_2$C$_6$X$_4$ (X=H,F)", *J. Am. Chem. Soc.*, 1999, 121, 3244–3245.
Rosevear, J. et al., *Aust. J. Chem.*, 1985, 38, 1163–1176.
Stürmer, R., *Angew. Chem. Int. Ed.*, 1999, 38, 3307–3308.
Advanced Organic Chemistry, March, Wiley, New York, 1992 (4$^{th}$ Ed.).
Sernetz, Friedrich G. et al., "Copolymerization of Ethene with Styrene Using Methylaluminoxane—Activated Bis(phenolate) Complexes", *Macromolecules*, 1997 30(6) 1562–1569.

* cited by examiner

*Primary Examiner*—Robert D. Harlan

(57) ABSTRACT

Metal-ligand complexes that are useful as precursors to catalysts for the polymerization of olefins are provided. Certain of the catalysts are particularly effective at polymerizing ethylene and styrene into copolymers having novel properties, including a low molecular weight and close comparison between vinyl and methyl end groups.

21 Claims, No Drawings

ETHYLENE-STYRENE COPOLYMERS AND PHENOL-TRIAZOLE TYPE COMPLEXES, CATALYSTS, AND PROCESSES FOR POLYMERIZING

This application is a divisional application of U.S. patent application Ser. No. 10/121,300, filed on Apr. 12, 2002, now issued as U.S. Pat. No. 6,794,514 to Brümmer et al.

FIELD OF THE INVENTION

The present invention relates to novel polymers. The present invention also relates to metal-ligand complexes, catalysts and catalyst compositions that are active for polymerizing olefins. The invention also relates to certain of these catalysts and catalyst compositions that polymerize ethylene and styrene to a product having unique properties.

BACKGROUND OF THE INVENTION

Ancillary (or spectator) ligand-metal coordination complexes (e.g., organometallic complexes) and compositions are useful as catalysts, additives, stoichiometric reagents, monomers, solid-state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, *Adv. Organometallic Chem.,* 1991, Vol. 32, pp. 325–387 and "Stereospecific Olefin Polymerization with Chiral Metallocene Catalysts", Brintzinger, et al., *Angew. Chem. Int. Ed. Engl.,* 1995, Vol.34, pp. 1143–1170, and the references therein, all of which is incorporated herein by reference.

One application for metallocene catalysts is producing ethylene copolymers. For example, PCT Application WO 00/37512 and published US patent application publication no. US 2001/0031843 A1 employ reaction product of zirconium tetrabenzyl and two equivalents of a phenol-triazole ligand with MMAO activation as catalyst for ethylene-hexene copolymerization (see Example 3). This application reports production of solid polyethylene, and states that the catalysts described are expected to produce HDPE (i.e., ethylene homopolymer) under ethylene-hexene copolymerization conditions (i.e., no incorporation of hexene).

As generally known to those of skill in the art of olefin polymerization, styrene is generally a more difficult comonomer to incorporate into an ethylene-α-olefin copolymer during copolymerization as compared with 1-hexene or 1-octene. See, e.g., Carlini et al., *polymer* 42 (2001) 5069–5078 ("The copolymerization of styrene with α-olefins by conventional Ziegler-Natta catalysts has been reported to occur with severe limitations.") Moreover, most known ethylene styrene copolymers are directed toward polymers where the styrene is present in a chain terminating position (see, e.g., U.S. Pat. Nos. 3,390,141 and 5,180,872 and Pellecchia et al., *Marcomolecules,* 2000, 33, 2807–2814 and EP 0 526 943). There remains a need to find new ethylene-styrene copolymers and catalysts for such copolymers. In addition there remains a need for new polyolefin catalysts, in general.

SUMMARY OF THE INVENTION

Given the state of the art, it was not expected to find a lower molecular weight ethylene-styrene copolymer with unique properties, preferably made during a bulk polymerization process using catalysts formed from phenol-triazole complexes of group 4 metals. It was surprising that such catalysts would incorporate styrene into an ethylene styrene copolymer as well as was found. This invention thus satisfies this desire for the production of ethylene styrene copolymers, particularly in a bulk solution process. Many of the phenol-triazole based catalysts disclosed herein demonstrate high activity for ethylene-styrene copolymerization. These catalysts typically produce low molecular weight ethylene-styrene copolymers with styrene incorporated in the main chain of the polymer, which has a vinyl end group. These lower molecular weight copolymers represent a new and useful class of ethylene-styrene copolymers and may be generally described as liner α-olefins with phenyl substituents placed essentially randomly along the linear chain.

This invention discloses a new class of low molecular weight copolymers having unique bulk properties. This invention also discloses a novel polymerization process for the production of low molecular weight ethylene-styrene copolymers, as well as a novel class of catalysts and ligands making such catalysts. In some embodiments, the catalysts and ligands may be useful for polymerizing a wide variety of polymerizable monomers.

In some embodiments the polymers of this invention may be characterized by either of the general formulas I or II:

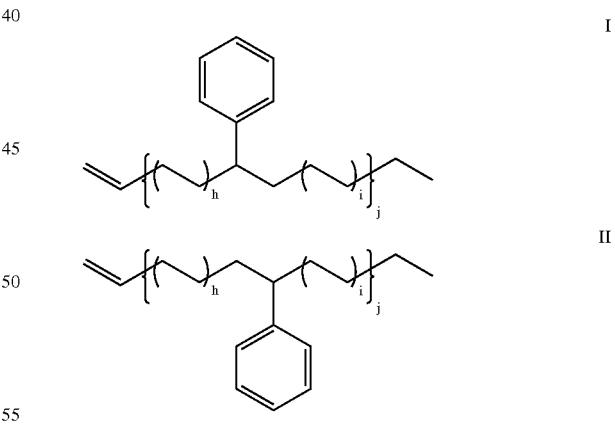

wherein h, i and j are each an integer greater than or equal to 1. The bulk polymers of this invention have a relatively low molecular weight, a relatively narrow molecular weight distribution and an end analysis by NMR that shows a close association between the numbers of vinyl and methyl end-groups. The bulk polymers also show that the styrene monomer incorporated into the chain is typically not at one of the ends of the polymer, but are randomly distributed along the polymer backbone.

Other aspects of this invention include a method of polymerizing ethylene and styrene to form a copolymer using a catalyst. The catalysts of this invention generally comprise a composition or metal-ligand complex, with the ligand employed either being a phenol with a triazole or similar substituent ortho to the hydroxy. In those embodiments where a composition is employed, the ligands are combined with a metal precursor compound at a desired molar ratio (such as 2:1), with the metal precursor comprising a group 4 metal (i.e., zirconium, hafnium or titanium). In those embodiments where a metal-ligand complex is used, the complex may be isolated or formed in situ. The catalyst typically includes an activator, combination of activators or activating technique. The ligands useful in this invention can be generally described by the general formula:

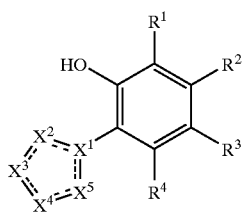

wherein $X^1$ and $X^2$ are N, and $X^3$, $X^4$, and $X^5$ are independently selected from the group consisting of N and $CR^{15}$, where $R^{15}$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, and combinations thereof, provided that at least one and not more than two of $X^3$, $X^4$, and $X^5$ are N; optionally, $X^3$ and $X^4$ may be joined to form a fused ring system having up to 50 atoms, not counting hydrogen atoms; and $R^1$, $R^2$, $R^3$ and $R^4$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, nitro, and combinations thereof, with the exception that $R^1$ may not be hydrogen, and optionally two or more of $R^1$, $R^2$, $R^3$ and $R^4$ (for example $R^1$ and $R^2$, or $R^2$ and $R^3$, or $R^3$ and $R^4$) may be joined to form a fused ring system having up to 50 atoms, not counting hydrogen atoms.

In other aspects of this invention, certain of the ligands and certain of the metal-ligand complexes are novel. These novel ligands and/or metal complexes can form catalysts useful for the polymerization of a variety of monomers, including α-olefins in general.

Further aspects and objects of this invention will be evident to those of skill in the art upon review of this specification.

DETAILED DESCRIPTION OF THE INVENTION

The inventions disclosed herein include metal-ligand complexes and compositions, which are useful as catalysts for polymerization reactions, and in a specific embodiment, polymerization of ethylene and styrene into copolymers having a novel combination of properties and/or structures.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

Also as used herein "styrene" is intended to include substituted versions of styrene, such as para-t-butyl-styrene.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent, which may be a single aromatic ring or multiple aromatic rings, which are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

"Substituted heteroaryl" refers to heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $—OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the $—SiZ^1Z^2Z^3$ radical, where each of $Z^1$, $Z^2$, and $Z^3$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the $—BZ^1Z^2$ group, where each of $Z^1$ and $Z^2$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group $—PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

As used herein, the term "phosphine" refers to the group: $PZ^1Z^2Z^3$, where each of $Z^1$, $Z^3$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group $—NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "amine" is used herein to refer to the group: $NZ^1Z^2Z^3$, where each of $Z^1$, $Z^2$ and $Z^2$ is independently selected from the group consisting of-hydrogen, alkyl, substituted alkyl, cycloalkyl, substituted cycloalkyl, heterocycloalkyl, substituted heterocycloalkyl, aryl (including pyridines), substituted aryl, heteroaryl, substituted heteroaryl, alkoxy, aryloxy, silyl and combinations thereof.

The term "thio" is used herein to refer to the group $—SZ^1$, where $Z^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group $—SeZ^1$, where $Z^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "halo" refers to Cl, F, Br or I bonded to a carbon and "halide" refers to Cl, F, Br or I bonded to a metal.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylide, oxazolinyl, cyclohexenyl, acetyl and the like.

Ligands and Compositions

The ligands useful in this invention are generally characterized by the general formula:

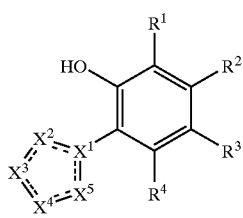

(III)

wherein $X^1$ and $X^2$ are N, and $X^3$, $X^4$, and $X^5$ are independently selected from the group consisting of N and $CR^{15}$, where $R^{15}$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, and combinations thereof, provided that at least one and not more than two of $X^3$, $X^4$, and $X^5$ are N; optionally, $X^3$ and $X^4$ may be joined to form a fused ring system having up to 50 atoms, not counting hydrogen atoms.

In general, $R^1$, $R^2$, $R^3$ and $R^4$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, nitro, and combinations thereof, with the exception that $R^1$ may not be hydrogen, and optionally two or more of $R^1$, $R^2$, $R^3$ and $R^4$ (for example $R^1$ and $R^2$, or $R^2$ and $R^3$, or $R^3$ and $R^4$) may be joined to form a fused ring system having up to 50 atoms, not counting hydrogens. In formula (III), however, $R^2$ and $R^4$ are both hydrogen or are joined in a fused ring system, as just described.

In formula (III) above, the presence of one solid line and one dashed line between each of the X groups in the heterocycle ring ($X^1$ to $X^5$) is intended to indicate that each of the bonds between any two adjacent X groups may be a single bond or a double bond or a bond with bond order intermediate between single and double, such as the delocalized bonding in an aromatic ring.

In more specific embodiments, $R^1$ and $R^3$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, halo, silyl, boryl, phosphino, amino, thio, seleno, nitro, and combinations thereof, with the exception that $R^1$ may not be hydrogen. Also, $R^2$ and $R^4$ are hydrogen, or two or more of $R^1$, $R^2$, $R^3$ and $R^4$ (for example $R^1$ and $R^2$, or $R^2$ and $R^3$, or $R^3$ and $R^4$) may be joined to form a fused ring system having up to 50 atoms, not counting hydrogen atoms.

In more specific embodiments the ligands useful in this invention may be characterized by the general formula:

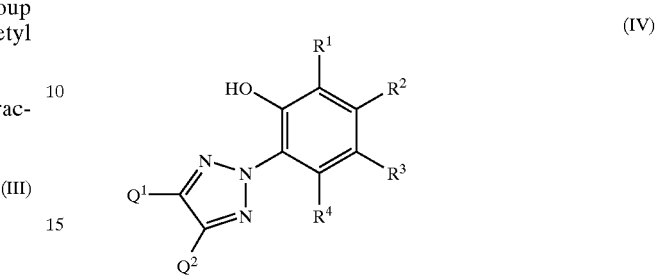

(IV)

wherein $R^1$, $R^2$, $R^3$ and $R^4$ are defined above (as for formula (III)), and $Q^1$ and $Q^2$ are independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, and combinations thereof; optionally, $Q^1$ and $Q^2$ may be joined to form a fused ring system having up to 50 atoms, not counting hydrogens.

In even more specific embodiments the ligands useful in this invention may be characterized by the general formula:

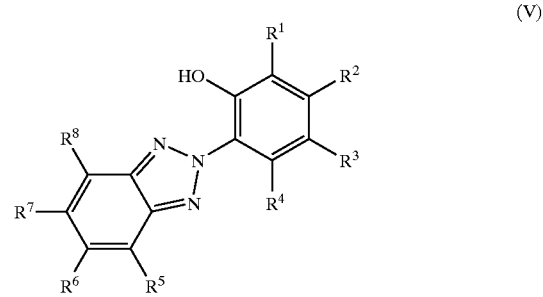

(V)

wherein $R^1$, $R^2$, $R^3$ and $R^4$ are defined above (as for formula (III)), and each of $R^5$, $R^6$, $R^7$ and $R^8$ is independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, nitro, and combinations thereof; optionally, two or more R groups (such as $R^5$ and $R^6$, or $R^6$ and $R^7$, or $R^7$ and $R^8$) may be joined to form a fused ring system having up to 50 atoms not counting hydrogen atoms.

In some preferred embodiments, one or both of $R^6$ and $R^7$ are halo substituents (F, Cl, Br or I), and in some more specific preferred embodiments one or both of $R^6$ and $R^7$ are chloro (Cl).

In other embodiments the ligands useful in this invention may be characterized by the general formula:

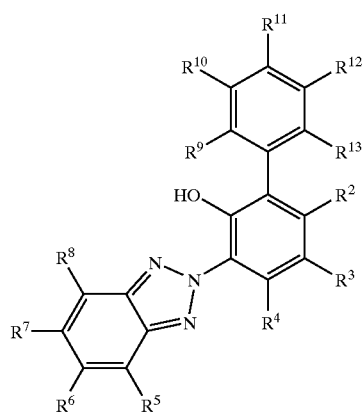

(VI)

wherein $R^3$, $R^5$, $R^6$, $R^7$ and $R^8$ are defined above, $R^2$ and $R^4$ are defined in their most general sense, and each of $R^9$, $R^{10}$, $R^{11}$, $R^{12}$ and $R^{13}$ is independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, nitro, and combinations thereof; optionally, two or more R groups (such as $R^9$ and $R^{10}$, or $R^{12}$ and $R^{13}$) may be joined to form a fused ring system having up to 50 atoms not counting hydrogen atoms. Examples of the fused ring systems include naphthyl, phenanthrenyl, and anthracenyl.

In further more specific embodiments the ligands useful in this invention may be characterized by the general formula:

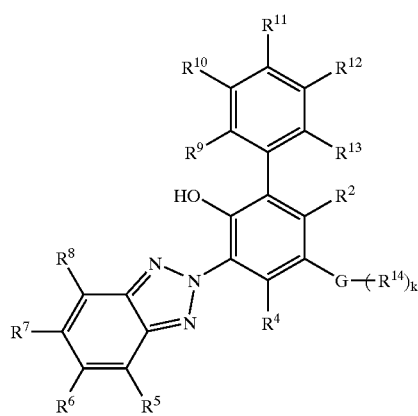

(VII)

wherein $R^2$, $R^4$, $R^5$, $R^6$, $R^7$, $R^8$, $R^9$, $R^{10}$, $R^{11}$, $R^{12}$ and $R^{13}$ are as defined above (as in for example formula (VI)), G is selected from the group consisting of O, S, N and P, k is 1 when G is O or S, k is 2 when G is N or P, and $R^{14}$ is selected from the group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, silyl, and combinations thereof.

In formulas (III) (IV), (V), (VI) and (VII) above, even though the bonding in the phenol, triazole, benzotriazole and aryl groups is drawn as single or doubles bonds, one of skill in the art will understand that the bonding may be partially of fully delocalized in nature and the bond orders shown in these formulas are intended to be illustrative and not limiting.

In more specific embodiments of the above ligands, where applicable, specific R groups may be narrowed to particularly preferred embodiments, such as those embodiments listed in the definitions. In some preferred embodiments, $R^2$ and $R^4$ are both hydrogen.

Specific ligands useful in this invention include:

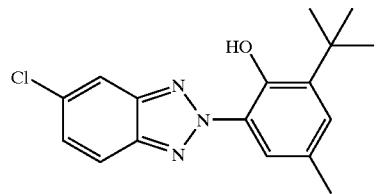

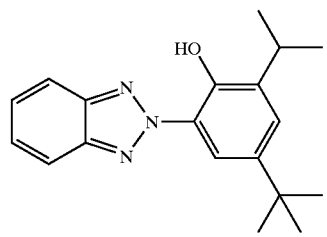

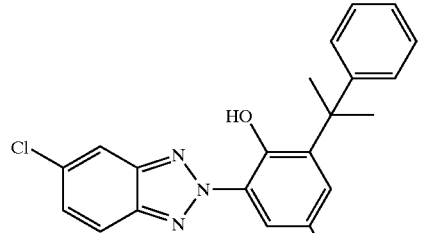

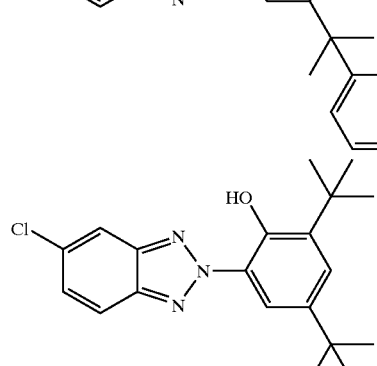

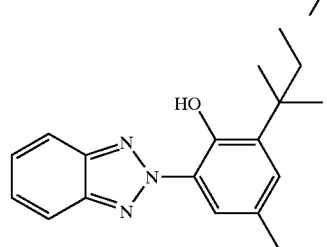

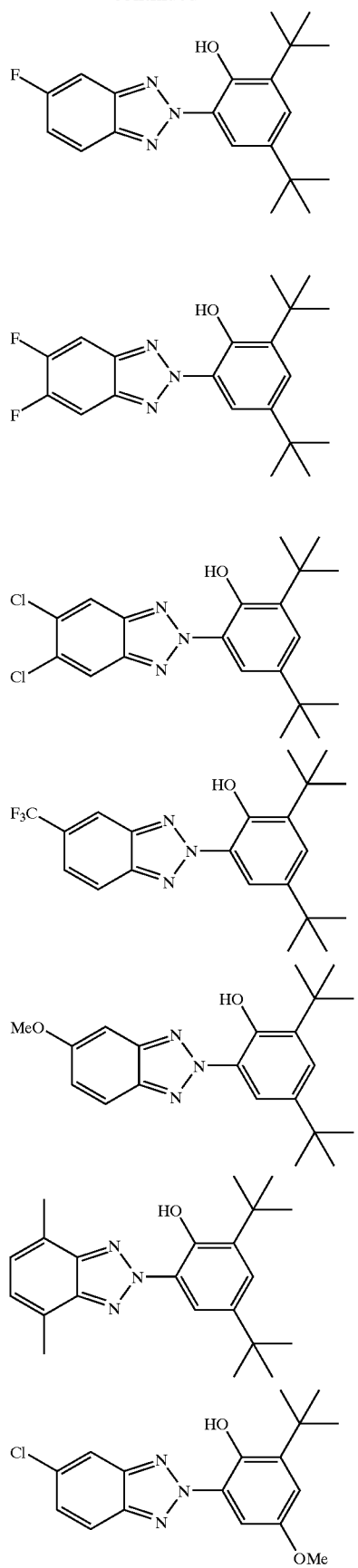
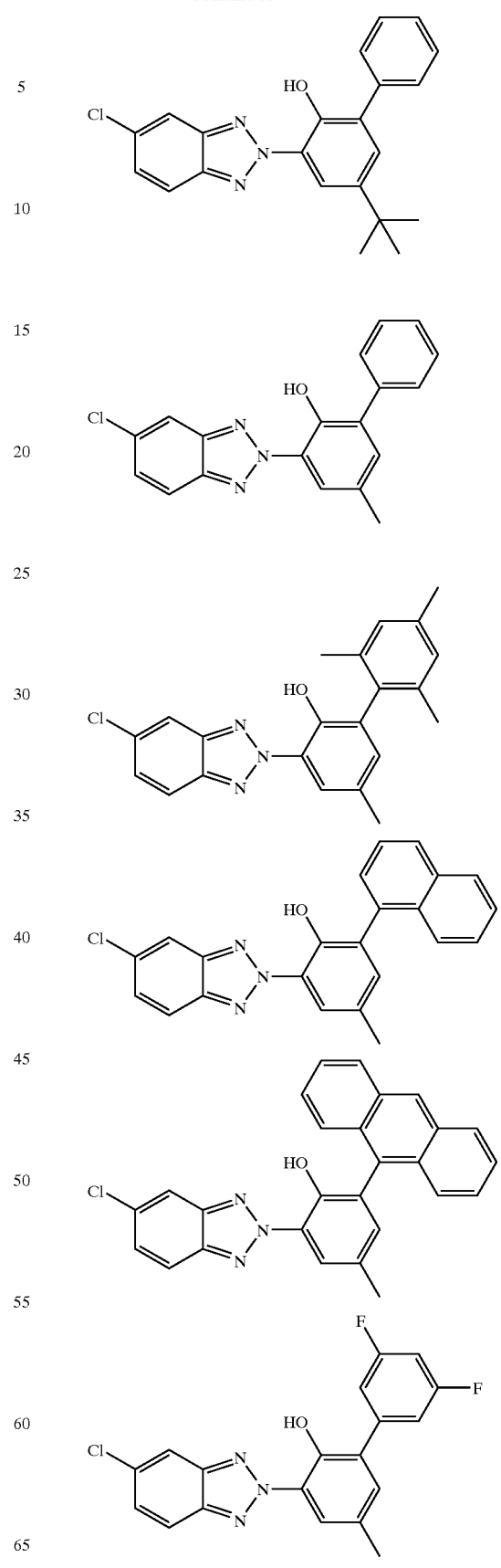

-continued

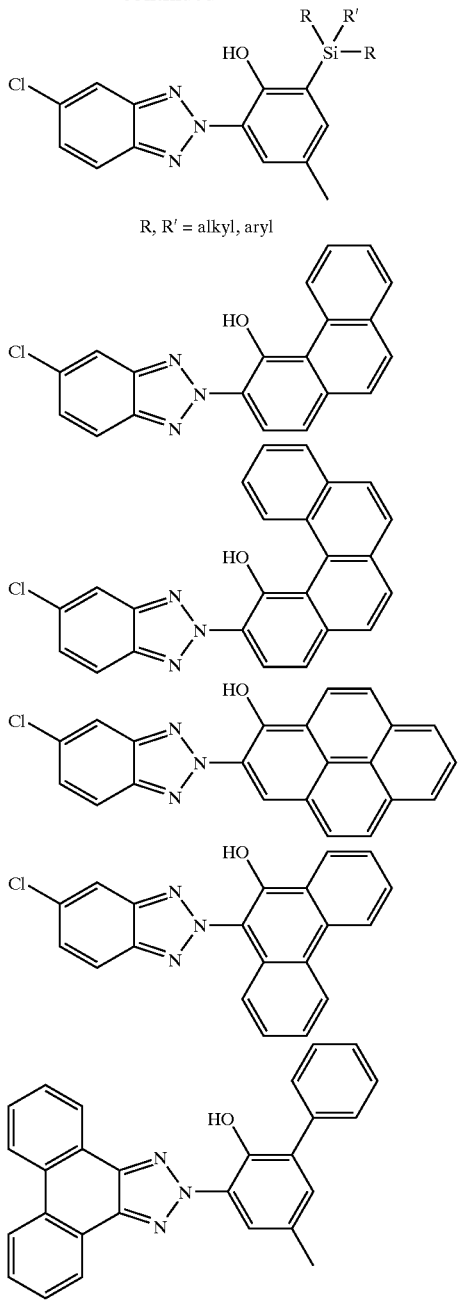

R, R' = alkyl, aryl

These ligands may be prepared using known procedures or obtained from commercial sources (such as Aldrich Chemicals; see, for example, Advanced Organic Chemistry, March, Wiley, New York 1992 (4$^{th}$ Ed.)). Specifically, phenol benzotriazole ligands were prepared according to J. Rosevear and J. F. K. Wilshire, *Aust. J. Chem.* 1985, 38, 1163–1176: Substituted nitroanilines were transformed into the corresponding diazo compounds and then reacted with substitued phenols under basic conditions. The resulting diazo dyes were cyclized under reductive conditions. Substituted phenols were obtained from either 2-bromo-4-methylanisole or 4-bromo-2-chlorophenol, respectively, using standard cross coupling procedures (R. Stürmer, *Angew. Chem. Int. Ed.* 1999, 38, 3307–3308).

Once the desired ligand is formed, it may be combined with a metal atom, ion, compound or other metal precursor compound. In some applications, the ligands of this invention will be combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

The metal precursor compounds may be characterized by the general formula M(L)$_n$ where M is zirconium, titanium or hafnium and each L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, hydrido, allyl, diene, seleno, phosphino, carboxylates, thio, 1,3-dionates, oxalates, carbonates, nitrates, sulphates, and combinations thereof, and n is 1, 2, 3, or 4. The metal precursors may be monomeric, dimeric or higher orders thereof. In addition, Lewis base adducts of these compounds are also suitable as metal precursors. Suitable Lewis bases include ethers, amines, thioethers, phosphines and the like.

Specific examples of suitable zirconium and hafnium precursors include, but are not limited to $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, and $Zr(N(SiMe_3)_2)_2Cl_2$, $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$. Lewis base adducts of these examples are also suitable as metal precursors, for example, ethers, amines, thioethers, phosphines and the like are suitable as Lewis bases.

The ligand to metal precursor compound ratio is typically in the range of about 0.01:1 to about 100:1, more preferably in the range of about 0.1:1 to about 10:1, even more preferable in the range 1:1 to 2:1, and most preferably around 2:1.

The catalysts of this invention may also comprise a composition comprising a ligand and metal precursor (each of which are as described above), without isolation of the metal-ligand complex. This composition can be activated as described below.

The ligands, complexes or catalysts may be supported on an organic or inorganic support. Suitable supports include silicas, aluminas, clays, zeolites, magnesium chloride, polyethyleneglycols, polystyrenes, polyesters, polyamides, peptides and the like. Polymeric supports may be cross-linked or not. Similarly, the ligands, complexes or catalysts may be supported on similar supports known to those of skill in the art. In addition, the catalysts of this invention may be combined with other catalysts in a single reactor and/or employed in a series of reactors (parallel or serial) in order to form blends of polymer products.

In another embodiment, the non-leaving group (or ancillary) phenol-heterocycle or phenol-triazole ligands herein may be bridged together by a bridging group, with the bridging group linking two phenol or two heterocycle moieties of the ligands. Bridging groups include those having from 1 to 6 atoms in the backbone of the bridge and include moieties such as -(EZ$^1$Z$^2$)$_{n''}$- where each E is independently C or Si, n'' is an integer from 1 to 6 and where the Z groups are defined above, -(EZ$^1$Z$^2$)$_{m''}$-(Ar)$_{p''}$-(EZ$^1$Z$^2$)$_{q''}$- where Ar is an aryl or substituted aryl or heteroaryl or substituted heteroaryl group, m'', p'' and q'' are independently 1 or 2.

Metal Complexes

This invention, in part, relates to new metal-ligand complexes. Generally, the ligand is mixed with a suitable metal precursor compound prior to or simultaneously with allowing the mixture to be contacted with the reactants (e.g., monomers). When the ligand is mixed with the metal precursor compound, a metal-ligand complex may be formed, which may be a catalyst or may need to be activated to be a catalyst.

Metal-ligand complexes, which are useful for the production of the styrene-ethylene copolymers discussed herein, are those, generally having two non-leaving group (or ancillary) phenol-heterocycle or phenol-triazole ligands attached to the metal center. In other words, there is a 2:1 ligand to metal ratio intended (although such ratio may not be exact). Such metal complexes may be characterized by the following general formula:

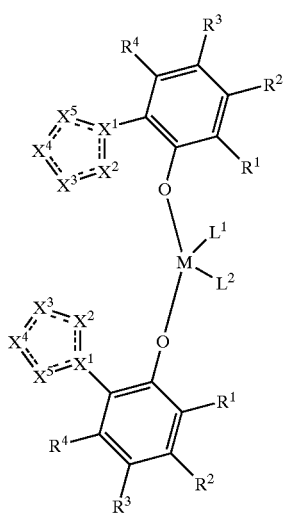

(VIII)

wherein R$^1$, R$^2$, R$^3$, R$^4$, X$^1$, X$^2$, X$^3$, X$^4$, and X$^5$ are defined as in formula (III), above, and M is zirconium, titanium or hafnium; and L$^1$ and L$^2$ are independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, thio, boryl, silyl, amino, hydrido, allyl, seleno, phosphino, carboxylates, and combinations thereof.

Lewis base adducts of the formula (VIII) are also suitable as metal-ligand complexes, for example, ethers, amines, thioethers, phosphines and the like are suitable as Lewis bases. The metal-ligand complexes may be a catalyst or may need to be activated to be a catalyst.

Formula (VIII) is intended to include the option of dative bonding between X$^2$ and M for one or both of the phenol-heterocycle ligands, as shown below in general formulas (VIII)a (showing 5 bonds from ligands to the metal) and (VIII)b (showing 6-coordinate metal-ligand complex):

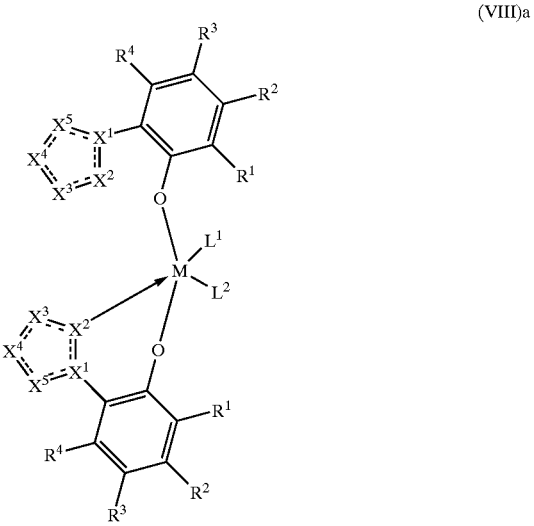

(VIII)a

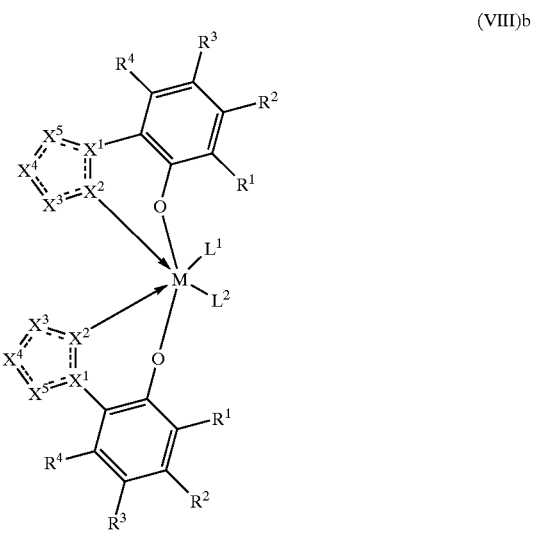

(VIII)b

For metal-ligand complexes of the general type described by formula (VIII)b, in which there are six (6) bonds to the metal M, the ligands might be arranged around the metal in a variety of orientations to produce several possible different isomers, some examples of which are shown diagrammatically below, in which the ligands are represented by the O—X$^2$ groups:

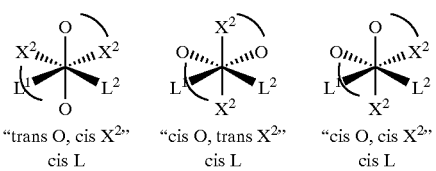

"trans O, cis X$^2$"        "cis O, trans X$^2$"        "cis O, cis X$^2$"
    cis L                        cis L                         cis L

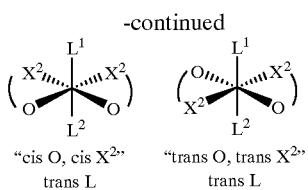

"cis O, cis X²"
trans L

"trans O, trans X²"
trans L

In even more specific embodiments the metal-ligand complexes useful in this invention may be characterized by the general formula:

(IX)

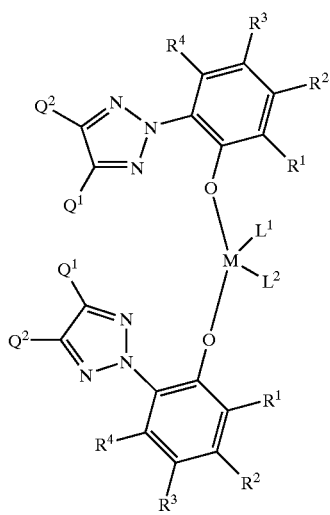

wherein $R^1, R^2, R^3, R^4, Q^1, Q^2, M, L^1$ and $L^2$ are defined as above, e.g., as in formula (IV) and (VIII).

The general formula (IX) is intended to include the option of dative bonding between one N and M for one or both of the phenol-triazole ligands, as shown below in general formulas (IX)a (showing 5 bonds to the metal) and (IX)b (showing 6 bonds to the metal):

(IX)a

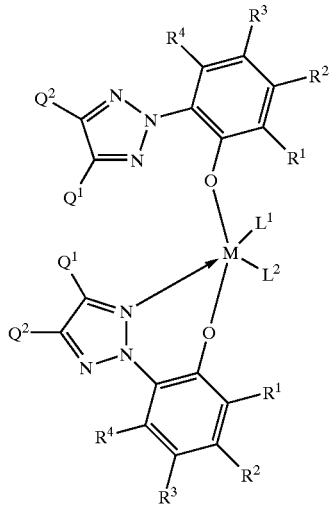

(IX)b

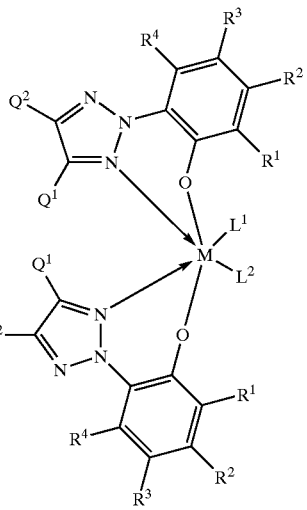

For metal-ligand complexes of the general type described by formula (IX)b, in which the metal M has six bonds from ligands, the ligands can be arranged around the metal in a variety of orientations to produce several possible different isomers, some examples of which are shown diagrammatically below, in which the non-leaving group (or ancillary) phenol-triazole ligands are represented by the O—N groups:

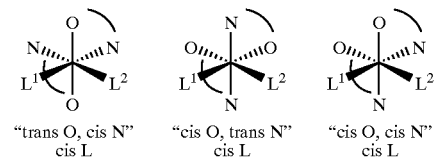

"trans O, cis N"
cis L

"cis O, trans N"
cis L

"cis O, cis N"
cis L

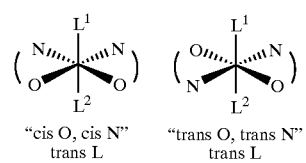

"cis O, cis N"
trans L

"trans O, trans N"
trans L

In other embodiments the metal-ligand complexes of this invention may be characterized by the general formula:

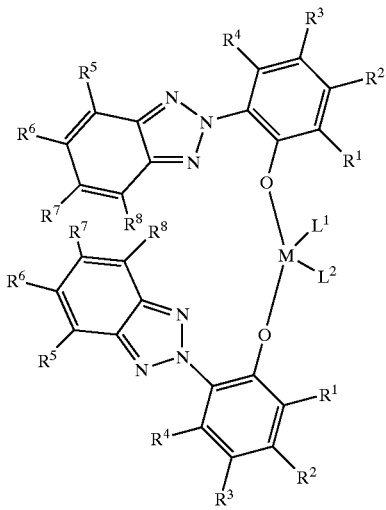

(X)

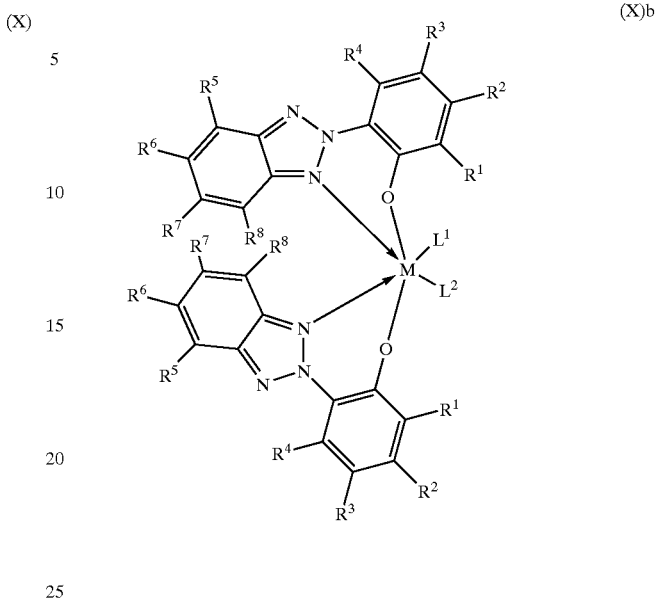

(X)b wherein $R^1$, $R^2$, $R^3$ $R^4$ $R^5$, $R^6$, $R^7$, $R^8$, M, $L^1$ and $L^2$ are defined above, e.g., as in formula (V) and (VIII).

The general formula (X) is intended to include the option of dative bonding between one N and M for one or both of the phenol-benzotriazole ligands, in the same fashion as shown above, and as shown in general formulas (X)a (showing 5 bonds to the metal) and (X)b (showing 6 bonds to the metal):

For metal-ligand complexes of the general type described by formula (X)b, in which the metal M has six bonds from ligands, the ligands can be arranged around the metal in a variety of orientations to produce several possible different isomers, some examples of which are shown diagrammatically above, in which the non-leaving group (or ancillary) phenol-benzotriazole ligands are represented by the O—N groups.

In other embodiments the metal-ligand complexes of this invention may be characterized by the general formula:

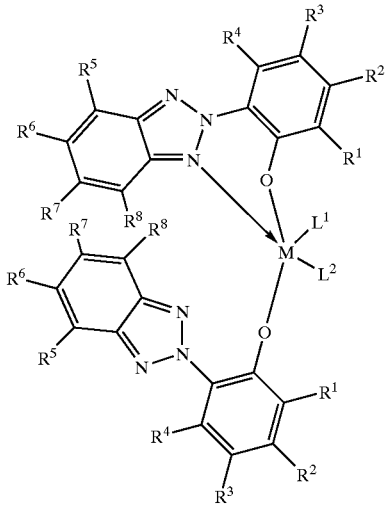

(X)a

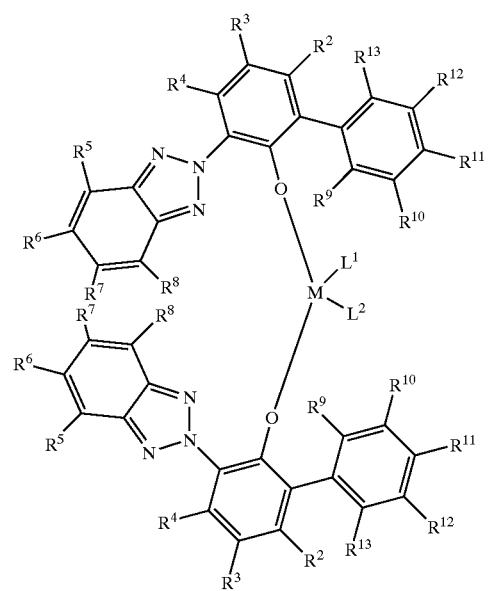

(XI)

wherein $R^2$, $R^3R^4R^5$, $R^6$, $R^7$, $R^8$, $R^9$, $R^{10}$, $R^{11}R^{12}R^{13}$, M, $L^1$ and $L^2$ are defined above, e.g., as in formula (VI) and (VIII). The general formula (XI) is intended to include the option of dative bonding between one N and M for one or both of the non-leaving group phenol-benzotriazole ligands, in the same fashion as shown above, in general formulas (XI)a (showing 5 bonds to the metal) and (XI)b (showing 6 six bonds to the metal):

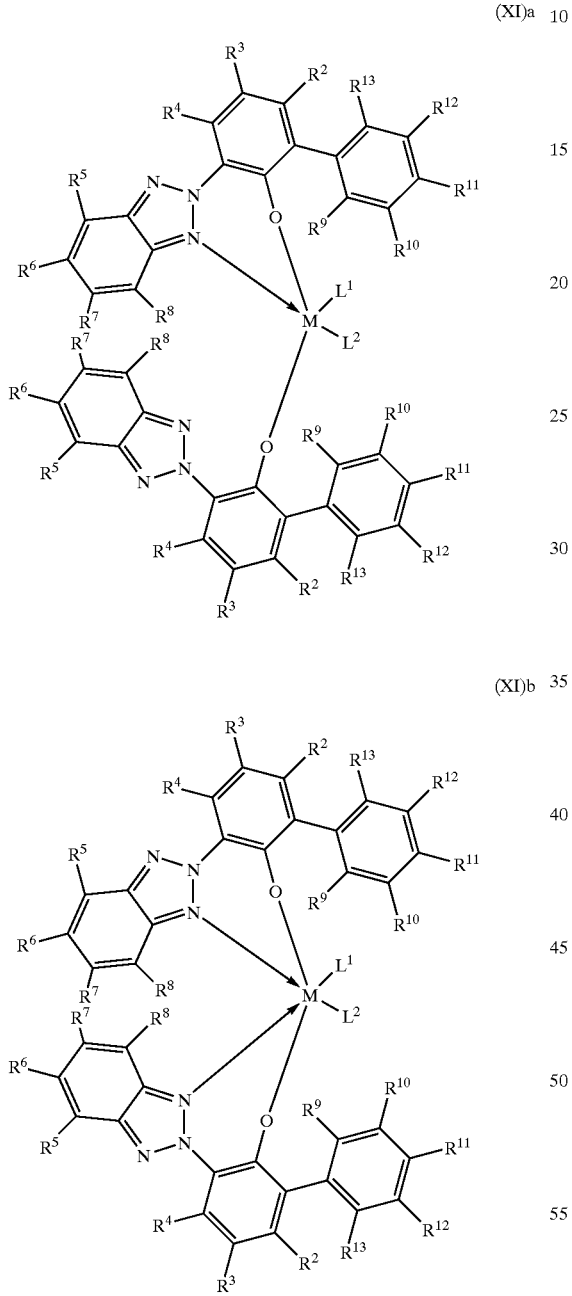

(XI)a (XI)b

For metal-ligand complexes of the general type described by formula (XI)b, in which the metal M has six bonds from ligands, the ligands can be arranged around the metal in a variety of orientations to produce several possible different isomers, some examples of which are shown diagrammatically above, in which the non-leaving group (or ancillary) phenol-benzotriazole ligands are represented by the O—N groups.

In still further even more specific embodiments the metal-ligand complexes useful in this invention may be characterized by the general formula:

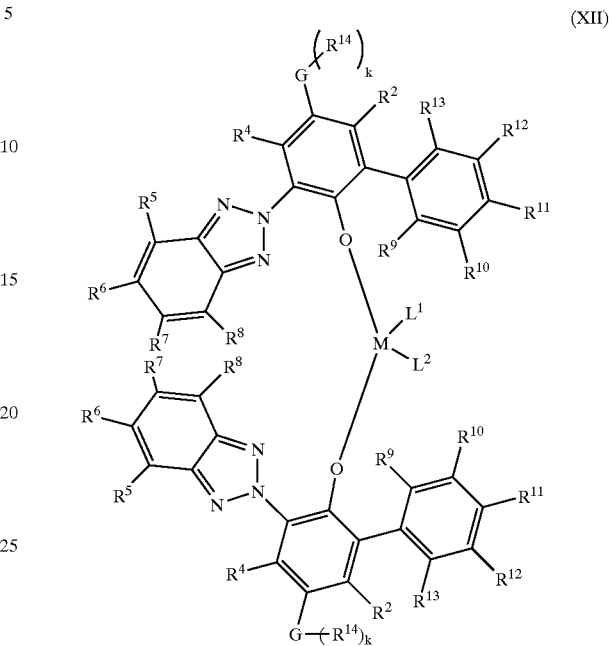

(XII)

wherein $R^2, R^4R^5, R^6, R^7, R^8, R^9, R^{10}, R^{11}R^{12}R^{13}, R^{14}, G, k$, M, $L^1$ and $L^2$ are defined above, e.g., as in formula (VI) and (VIII). The general formula (XII) is intended to include the option of dative bonding between one N and M for one or both of the non-leaving group phenol-benzotriazole ligands, in the same fashion as shown above, in general formulas (XII)a (showing 5 bonds to the metal) and (XII)b (showing 6 six bonds to the metal):

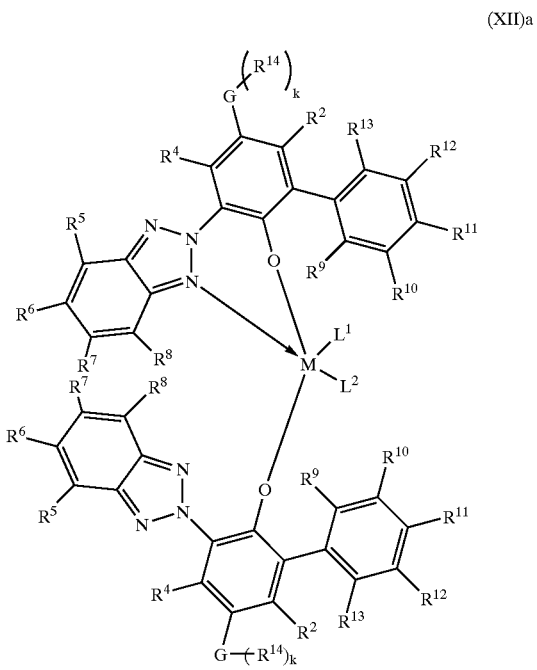

(XII)a

-continued

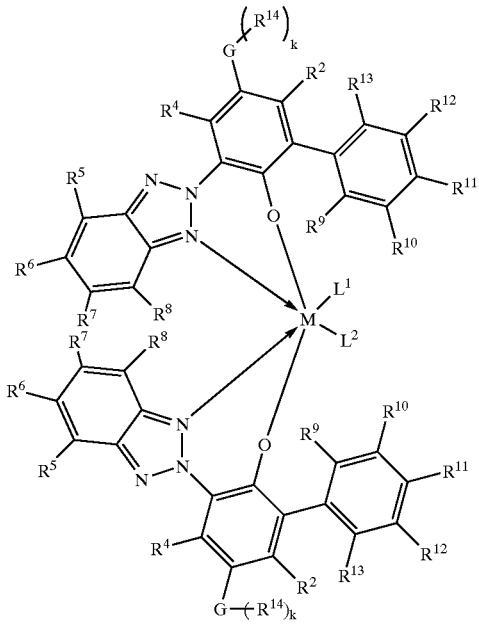

(XII)b

For metal-ligand complexes of the general type described by formula (XII)b, in which the metal M has six bonds from ligands, the ligands can be arranged around the metal in a variety of orientations to produce several possible different isomers, some examples of which are shown diagrammatically above, in which the non-leaving group (or ancillary) phenol-benzotriazole ligands are represented by the O—N groups. Lewis base adducts of the formulas (VIII), (IX), (X), (XI), and (XII) are also suitable as metal-ligand complexes, for example, ethers, amines, thioethers, phosphines and the like are suitable as Lewis bases.

The metal complexes of this invention, and useful in this invention, can be formed by techniques known to those of skill in the art.

Polymerization Activators/Additives

The metal-ligand complexes and compositions are active catalysts typically in combination with a suitable activator, combination of activators, activating technique or activating package. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453, 410, 5,153,157, 5,064,802, and EP-A-277,004. In particular, ionic or ion forming activators are preferred.

Suitable ion forming compounds useful as an activator in one embodiment of the present invention comprise a cation that is a Bronsted acid capable of donating a proton, and an inert, compatible, non-interfering, anion, A⁻. Preferred anions are those containing a single coordination complex comprising a charge-bearing metal or metalloid core. Mechanistically, said anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion, are available commercially.

Preferably such activators may be represented by the following general formula:

$$(L^*\text{-}H)_d^+(A^{d-})$$

wherein, L* is a neutral Lewis base; (L*-H)⁺ is a Bronsted acid; $A^{d-}$ is a non-interfering, compatible anion having a charge of d−, and d is an integer from 1 to 3. More preferably $A^{d-}$ corresponds to the formula: $[M'^{3+}Q_h]^{d-}$ wherein h is an integer from 4 to 6; h−3=d; M' is an element selected from Group 13 of the Periodic Table of the Elements; and Q is independently selected from the group consisting of hydride, dialkylamido, halide, alkoxide, aryloxide, hydrocarbyl, and substituted-hydrocarbyl radicals (including halosubstituted hydrocarbyl, such as perhalogenated hydrocarbyl radicals), said Q having up to 20 carbons. In a more preferred embodiment, d is one, i.e., the counter ion has a single negative charge and corresponds to the formula A⁻.

Activators comprising boron or aluminum which are particularly useful in the preparation of catalysts of this invention may be represented by the following general formula:

$$[L^*\text{-}H]^+[JQ_4]^-$$

wherein: L* is as previously defined; J is boron or aluminum; and Q is a fluorinated $C_{1-20}$ hydrocarbyl group. Most preferably, Q is independently selected from the group selected from the group consisting of fluorinated aryl group, especially, a pentafluorophenyl group (i.e., a $C_6F_5$ group) or a 3,5-bis(CF$_3$)$_2$C$_6$H$_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(secbutyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate and N,N-dimethylanilinium tetrakis-(2,3,4,6-tetrafluorophenyl) borate; dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphosphonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate; and N,N-dimethylanilinium tetrakis(3,5-bis(trifluoromethyl)phenyl)borate. Additional examples of ammonium borate activators that may be usefully employed as an activating co-catalyst in the preparation of the improved catalysts of this invention include examples where the [L*-H]+ cations are tri-substituted ammonium cations in which one or more of the substituents on the nitrogen is a long-chain alkyl group having from 10 to 40 carbon atoms, as described in U.S. Pat. No. 5,919,983, WO 01/48035 A2 and WO 02/02577, each of which are incorporated herein by reference. Some preferred embodiments include activators of the type [MeNR$_2$H]$^+$[B(C$_6$F$_5$)$_4$]$^-$ and [PhNR$_2$H]$^+$[B(C$_6$F$_5$)$_4$]$^-$, where each R is independently (CH$_2$)$_n$CH$_3$ where n is 13, 15 or 17, and more specifically [MeN((CH$_2$)$_{17}$CH$_3$)$_2$H]$_+$[B(C$_6$F$_5$)$_4$]$^-$, and [PhN((CH$_2$)$_{17}$CH$_3$)$_2$H]$^+$[B(C$_6$F$_5$)$_4$]$^-$. Preferred [L*-H]$^+$ cations are N,N-dimethylanilinium and N,N-di(n-alkyl) anilinium where each alkyl is independently (CH$_2$)$_n$CH$_3$ where n is 13, 15 or 17. Preferred anions are tetrakis(3,5-bis(trifluoromethyl)phenyl)borate and tetrakis (pentafluorophenyl)borate.

Other suitable ion forming activators comprise a salt of a cationic oxidizing agent and a non-interfering, compatible anion represented by the formula:

$$(Ox^{e+})_d(A^{d-})_e$$

wherein: $Ox^{e+}$ is a cationic oxidizing agent having a charge of e+, e is an integer from 1 to 3; and $A^{d-}$, and d are as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound that is a salt of a carbenium ion or silyl cation and a non-interfering, compatible anion represented by the formula:

wherein: $©^+$ is a $C_{1-100}$ carbenium ion or silyl cation; and $A^-$ is as previously defined. A preferred carbenium ion is the trityl cation, i.e. triphenylcarbenium. The silyl cation may be characterized by the formula $Z^1Z^2Z^3Si^+$ cation, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl and combinations thereof.

Other suitable activating cocatalysts comprise a compound that is a salt, which is represented by the formula $(A^{*+a})_b(Z^*J^*_j)^{-c}_d$ wherein $A^*$ is a cation of charge +a; $Z^*$ is an anion group of from 1 to 50, preferably 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that axb is equal to cxd. See, WO 99/42467, which is incorporated herein by reference. In other embodiments, the anion portion of these activating cocatalysts may be characterized by the formula $((C_6F_5)_3M''''-LN-M''''(C_6F_5)_3)^-$ where M'''' is boron or aluminum and LN is a linking group, which is preferably selected from the group consisting of cyanide, azide, dicyanamide and imidazolide. The cation portion is preferably a quaternary amine. See, e.g., LaPointe et al., *J. Am. Chem. Soc.* 2000, 122, 9560–9561, which is incorporated herein by reference.

In addition, suitable activators include Lewis acids, such as those selected from the group consisting of tris(aryl) boranes, tris(substituted aryl)boranes, tris(aryl)alanes, tris (substituted aryl)alanes, including activators such as tris (pentafluorophenyl)borane. Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-[B(C$_6$F$_5$)$_2$]$_2$C$_6$X$_4$ (X=H, F)", *J. Am. Chem. Soc.*, 1999, 121, 3244–3245, both of which are incorporated herein by reference. Other useful Lewis acids will be evident to those of skill in the art. In general, the group of Lewis acid activators are within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion forming activators. These compounds include a group 13 reagent that may be characterized by the formula $G^{13}R'_{3-p}D_p$ where $G^{13}$ is selected from the group consisting of B, Al, Ga, In and combinations thereof, p is 0, 1 or 2, each R' is independently selected from the group consisting of alkyl, substituted alkyl, cycloalkyl, heterocycloalkyl, heterocyclic and combinations thereof, and each D is independently selected from the group consisting of halide, hydride, alkoxy, aryloxy, amino, thio, phosphino and combinations thereof. Combinations of activators may be used. In other embodiments, the group 13 activator is an oligomeric or polymeric alumoxane compound, such as methylalumoxane and the known modifications thereof. In some embodiments a most preferred group 13 reagent is methylalumoxane or known modifications thereof. In these embodiments, it is preferable to use a minimal amount of group 13 reagent necessary for scavenging purposes (or none at all, if possible). In other embodiments, a divalent metal reagent may be used that is defined by the general formula $M'R'_{2-p'}D_{p'}$ and p' is 0 or 1 in this embodiment and R' and D are as defined above. M' is the metal and is selected from the group consisting of Mg, Ca, Sr, Ba, Zn, Cd and combinations thereof. In still other embodiments, an alkali metal reagent may be used that is defined by the general formula M"R' and in this embodiment R' is as defined above. M" is the alkali metal and is selected from the group consisting of Li, Na, K, Rb, Cs and combinations thereof.

The molar ratio of metal:activator (whether a composition or complex is employed as a catalyst) employed preferably ranges from 1:10,000 to 100:1, more preferably from 1:5000 to 10:1, most preferably from 1:10 to 10:1. In a preferred embodiment of the invention mixtures of the above compounds are used, particularly a combination of a group 13 reagent and an ion-forming activator. Currently, a most preferred combination is 1 equivalent of N,N-dimethylanilinium tetrakis(pentafluorophenyl) borate, and 0–5 equivalents of Akzo-Nobel MMAO-3A or Akzo-Nobel PMAO-IP.

Monomers/Polymers

The compositions, complexes and/or catalysts of this invention are particularly effective at polymerizing α-olefins (such as propylene, 1-butene, 1-pentene, 1-hexene, 1-heptene, 1-octene, and styrene), and copolymerizing ethylene with α-olefins (such as propylene, 1-butene, 1-pentene, 1-hexene, 1-heptene, 1-octene, and styrene).

In general monomers useful herein may be olefinically unsaturated monomers having from 2 to 20 carbon atoms either alone or in combination. Generally, monomers may include olefins, diolefins and unsaturated monomers including ethylene and $C_3$ to $C_{20}$ α-olefins such as propylene, 1-butene, 1-hexene, 1-octene, 4-methyl-1-pentene, 1-norbornene, styrene and mixtures thereof; additionally, 1,1-disubstituted olefins, such as isobutylene, 2-methyl-1-butene, 2-methyl-1-pentene, 2-ethyl-1-pentene, 2-methyl-1-hexene, 3-trimethylsilyl-2-methyl-1-propene, a-methyl-styrene, either alone or with other monomers such as ethylene or $C_3$ to $C_{20}$ α-olefins and/or diolefins. These definitions are intended to include cyclic olefins. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprises 1,5-dienes and other non-conjugated dienes. The styrene monomers may be unsubstituted or substituted at one or more positions on the aryl ring. The use of diolefins in this invention is typically in conjunction with another monomer that is not a diolefin. In some embodiments, acetylenically unsaturated monomers may be employed.

Novel polymers, copolymers or interpolymers may be formed having unique physical and/or melt flow properties. Polymers that can be prepared according to the present invention include propylene copolymers with at least one $C_4$–$C_{20}$ α-olefin, particularly 1-butene, 1-hexene, 4-methyl-1-pentene and 1-octene. The copolymers of propylene with at least one $C_4$–$C_{20}$ α-olefin comprise from about 0.1 wt. % higher olefin to about 60 wt. % higher olefin, more specifically from about 0.2 wt. % higher olefin to about 50 wt. % higher olefin and still more specifically from about 2 wt. % higher olefin to about 30 wt. % higher olefin.

In particular, certain embodiments of the catalysts of this invention have the capability of forming ethylene-styrene copolymers that have novel properties. These properties are determined in a manner known to those of skill in the art. These polymers are useful as additives to a variety of products, such as lubricants or waxes, as well as a macromer or oligomer additive to a further polymerization reaction. This latter application is due to the vinyl end group observed in these polymers. Herein, the use of "styrene" includes substituted styrenes.

The ethylene-styrene co-polymers of this invention have a relatively low molecular weight (less than about 10,000 and more specifically less than about 5,000, less than about 3,000 or less than about 1,000) combined with a relatively narrow molecular weight distribution (less than about 2.5 and more specifically less than about 2.0) and end-group, determined by NMR end-group analysis that show a ratio of methyl to vinyl in the range of from about 0.8:1 to about 1:0.8 and more specifically about 0.9:1 to about 1:0.9. The molecular weights may be weight averages or number averages. The end-group analysis is performed using proton nuclear magnetic resonance (NMR) techniques, which are relatively well known to those of skill in the art. The scientific error in this method is about 10–20%, given the ability to integrate the area under the peaks based on the relatively small peaks associated with the vinyl and methyl hydrogen atoms as compared to the much larger peaks associated with the hydrogen atoms from the backbone of the polymer as well as given the close proximity of the shifts of the large methylene and small methyl peaks in the NMR spectrum. As those of skill in the art will appreciate, the peaks might be integrated more accurately with higher power NMR equipment. End analysis was performed in the manner discussed in the examples herein. The molecular weight and polydispersity are determined using size exclusion chromatography according to methods known to those of skill in the art, such as relative to linear polystyrene standards. See U.S. Pat. Nos. 6,294,388, 6,260,407, 6,175, 409, 6,296,771 and 6,265,226 each of which is incorporated herein by reference.

The co-polymers of this invention also show that the styrene monomer(s) incorporated into the chain do not lie just at one of the ends of the polymer, but are randomly distributed along the polymer backbone. In this regard, the polymers of this invention can be characterized by either of the general formulas I or II:

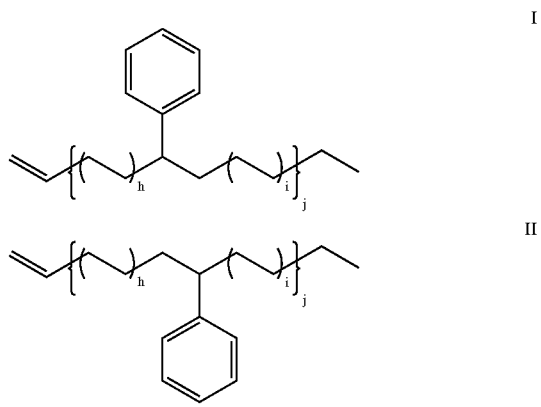

wherein h, i and j are each a number greater than or equal to 1. As those of skill in the art will appreciate, the numbers for h, i and j are dependant on the polymerization conditions chosen, including the amount of ethylene, amount of styrene, temperature, pressure, catalyst concentration and structure (including the activator(s) or activating package). Thus, both the ligand structure and choice of metal may influence the ethylene-styrene copolymerization catalyst performance and product properties. Under the specific polymerization conditions set forth in the examples, herein, some general trends included: (i) an aryl (e.g. phenyl, naphthyl or anthracenyl) substituent at the ortho position of the phenol ($R^1$) resulting, generally, in higher styrene incorporation into the copolymer product compared to a tert-butyl substituent at the ortho position, (ii) zirconium compositions and complexes have given higher activity, higher styrene incorporation, and lower molecular weight products than analogous hafnium compositions and complexes, (iii) halo, and especially chloro, substitution at the $R^6$ and $R^7$ positions of the above formulas (e.g., formula (V)) resulted in increased activity compared with H at these positions, (iv) methoxy (—OMe) substitution at the para position of the phenol ($R^3$) resulted in higher molecular weight product as compared to a tert-butyl substitution at this position, (v) an aryl (e.g. phenyl, naphthyl or anthracenyl) substituent at the ortho position of the phenol ($R^1$) resulted in longer catalyst lifetime at high temperature as compared to a tert-butyl substituent at the ortho position, there are ligand effects, metal effects and activator effects. Again these trends were found for the specific polymerization conditions employed herein and some or all of these trends might be modified under differing polymerization conditions.

Under the polymerization conditions chosen for the work undertaken in conjunction with this application, the degree of polymerization, which corresponds to the formula ((h+i+1)*j)+2, in a bulk sample is between 5 and 100, based on proton NMR analysis, more specifically between about 5 and 50 and even more specifically between about 5 and 25. In addition, the number of styrene monomers (j) in a bulk sample is between about 1 and 10, more specifically between about 1 and 5 and even more specifically between about 1 and 3. In alternative embodiments, the number of styrene monomers (j) in a bulk sample is between about 2 and 10 and more specifically between about 2 and 5. Testing to determine these numbers is typically by proton NMR, but other techniques known to those of skill in the art may also be employed.

The low molecular weight ethylene-styrene copolymers of this invention differ significantly from any previously reported ethylene-styrene copolymers or co-ligomers. The products of this invention have on average one or more styrene units incorporated per chain, such that the incorporated styrene unit is essentially randomly distributed along the length of the chain, such that the typical chain has a methyl (—$CH_3$) group at one end and a vinyl (—CH=$CH_2$) group at the other end. Thus the products of this invention are essentially linear α-olefins with phenyl substituents placed essentially randomly along the length of the chain.

Polymerization Systems

Polymerization can be carried out in the Ziegler-Natta or Kaminsky-Sinn methodology, including temperatures of from −100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, solution and high-pressure processes as known to those skilled in the art may also be used with supported catalysts of the invention.

As stated herein, a solution process is specified for certain benefits, with the solution process being run at a temperature above 90° C., more specifically at a temperature above 100° C., further more specifically at a temperature above 110° C. and even further more specifically at a temperature above 130° C. Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, and vinyltoluene (including all isomers alone or in admixture). Mixtures of the foregoing are also suitable.

Other additives that are useful in a polymerization reaction may be employed, such as scavengers, promoters, etc.

EXAMPLES

General: All organometallic reactions and polymerizations were performed under a purified argon or nitrogen atmosphere in a Vacuum Atmospheres glove box, using glassware previously dried in a vacuum oven at 150° C. overnight. All solvents used were anhydrous, de-oxygenated and purified according to known techniques. All ligands and metal precursors were prepared according to procedures known to those of skill in the art, e.g., under inert atmosphere conditions, etc. Ethylene/styrene copolymerizations were carried out in a parallel pressure reactor, which is fully described in pending U.S. patent applications Ser. No. 09/239,223, filed Jan. 29, 1999, and WO 00/09255, and U.S. Pat. No. 6,306,658 each of which is incorporated herein by reference.

High temperature Size Exclusion Chromatography (also known as gel permeation chromatography, "GPC") was performed using an automated "Rapid GPC" system as described in U.S. Pat. Nos. 6,175,409, 6,260,407, and 6,294,388 each of which is incorporated herein by reference. A series of two 30 cm×7.5 mm linear columns were used, with one column containing PLgel 10 um, MixB and the other column containing PLgel 5 um, MixC (available from Polymer Labs). The GPC system was calibrated using narrow polystyrene standards. The system was operated at a eluent flow rate of 1.5 mL/min and an oven temperature of 160° C. o-dichlorobenzene was used as the eluent. The polymer samples were dissolved 1,2,4-trichlorobenzene at a concentration of about 1 mg/mL. Between 40 μL and 200 μL of a polymer solution were injected into the system. The concentration of the polymer in the eluent was monitored using an evaporative light scattering detector. All of the molecular weight results obtained are relative to linear polystyrene standards.

Due to the low molecular weight of the ethylene-styrene copolymers produced by the catalyst systems of this invention, the resolution obtainable using the Rapid GPC system is limited by the lower exclusion limit of the column material. Because the molecular weights of the products of this invention are close to or below the lower size exclusion limit of the GPC columns, the Mw (weight average molecular weight) and especially the Mn (number average molecular weight) obtained by GPC are overestimated, while the polydispersity index (PDI=Mw/Mn) is underestimated, due to the lowest molecular weight fractions, which are below the size exclusion limit of the column material, eluting at approximately the same time as the higher molecular weight fractions which are at or slightly above the lower exclusion limit. The Mw and PDI shown in Table 4b illustrate this dependence of measured PDI on molecular weight.

The ratio of styrene to ethylene incorporated in the polymer products, represented as the mol % of styrene incorporated in the polymer (mol % incorporated styrene) was determined using $^1$H NMR spectroscopy (described below). The total styrene content of the polymer products (mol % total styrene), including both the styrene incorporated in the ethylene-styrene copolymer and any background homopolystyrene (PS) in the product sample, was determined using FTIR spectroscopy (linear regression method, described below).

$^1$H NMR method for determining mol % styrene incorporation: The ratio of styrene to ethylene incorporated in the polymer products, represented as the mol % (mole %) of styrene incorporated in the polymer was determined using $^1$H NMR spectroscopy. NMR samples were prepared as a solution of 10–40 mg of polymer in 0.4–0.5 mL of a 50/50 mixture by volume of 1,1,2,2-tetrachloroethane-d2 (TCE-d2) and tetrachloroethylene (Perchlor). Depending on the specific polymer, the sample was heated to completely dissolve the polymer. NMR was taken at a temperature between 20 and 90° C., such that the sample was fully dissolved. Proton NMR spectra of samples were acquired on a Bruker 300MHz NMR spectrometer. Abbreviations used below: iS=incorporated styrene (styrene incorporated into ethylene-styrene copolymer), aPS=atactic homopolystyrene, S=total styrene=iS+aPS, E=ethylene.

Data Analysis

The 1H NMR spectra are integrated using the following regions:

| | | |
|---|---|---|
| Styrene Aromatic = | 7.687–6.869 ppm = | region A |
| Atactic Polystyrene Aromatic = | 6.869–6.357 ppm = | region B |
| Vinyl Region = | 5.95–4.7 ppm = | region D |
| CH and CH$_2$ Aliphatic = | 3.212–1.0 ppm = | region E |
| Methyl = | 1.0–0.50 ppm = | region F |
| region C = | D + E + F | |

Calculations:

| | |
|---|---|
| Moles Styrene = | N(S) = (styrene region A + aPS region B)/5 |
| Moles aPS = | N(aPS) = (aPS region B)/2 |
| Moles Ethylene = | N(E) = (region C − N(S) * 3)/4 |
| N(iS)/N(E) = | N(S) − N(aPS)/N(E) |
| wt. % E = | N(E) * 28/(N(E) * 28 + N(S) * 104) |
| wt. % S (total) = | N(S) * 104/(N(E) * 28 + N(S) * 104) |
| wt. % aPS = | N(aPS) * 104/(N(E) * 28 + N(S) * 104) |
| wt. % iS = | (N(S) − N(aPS)) * 104/(N(E) * 28 + N(S) * 104) |
| mol % iS = | (N(iS)/N(E)) * 100/(1 + (N(iS)/N(E))) |
| N(vinyl) = | region D/3 |
| Chain length = | (N(E) + N(iS))/N(vinyl) |
| iS units per chain = | (N(S) − N(aPS))/N(vinyl) |
| E units per chain = | N(E)/N(vinyl) |
| Average molecular weight (Mn) = | iS units per chain * 104 + E units per chain * 28 |

FTIR method for determining mol % total styrene in product: FTIR was performed on a Bruker Equinox 55+ IR Scope II in reflection mode using a Pike MappIR accessory with 16 scans. The ratio of total styrene to ethylene was obtained from the ratio of band heights at 4330 cm$^{-1}$ and 1602 cm$^{-1}$. This method was calibrated using a set of ethylene-styrene copolymers with a range of known styrene content.

The total styrene content of the polymer products (mol % total styrene), includes both the styrene incorporated in the ethylene-styrene copolymer and any background homopolystyrene (PS) in the product sample. For the ethylene-styrene copolymerization conditions employed in Examples 3 and 4, the homopolystyrene background level is less than 3.5 wt % (1 mol %) and decreases (in percentage terms) with increasing product yield. For the products of this invention that were analyzed by $^1$H NMR, the homopolystyrene content was always below 3.5 weight % (for Example 3.6, product yield=82 mg) and more typically below 2 weight % for product yields or 100 mg or more.

Ligand Examples

The following ligands are used in some of these examples:

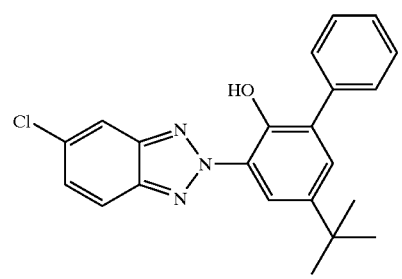

Ligand A

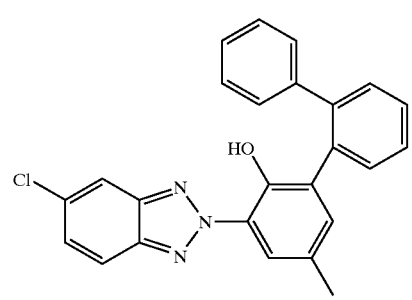

Ligand B

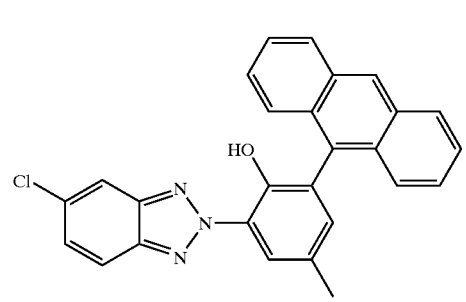

Ligand C

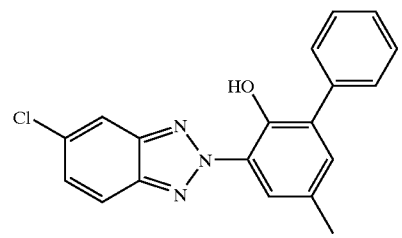

Ligand D

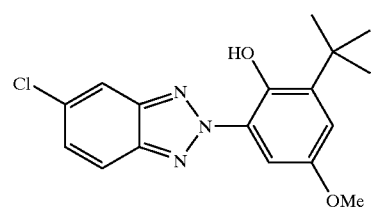

Ligand E

Ligand F

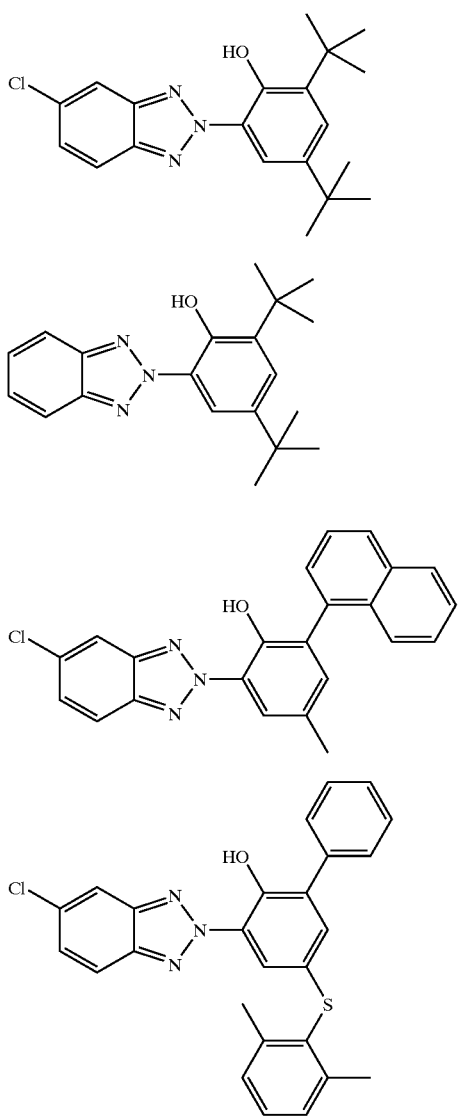

Ligand G

Ligand H

Ligand J

Ligand Synthesis Examples. General $^1$H NMR spectra were recorded on ligand solution in CDCl$_3$ and are reported relative to residual chloroform or TMS as the internal standard. Mass spectra were obtained by EI at 70 eV. Chromatography refers to flash chromatography on silica gel (230–400 mesh). All solvents used were anhydrous, and purified according to known techniques. All chemicals were purchased by Aldrich except for 4-tert.-butyl-2-phenylphenol (Avocado), xantphos and 2-(di-t-butylphosphino)biphenyl (Strem), and benzene boronic acid (Lancaster).

Example 1

Synthesis of Ligands

This example describes a general synthesis route that was used for the variety of ligands used herein, with the starting materials changed as appropriate.

Scheme 1: Synthesis of Ligand A

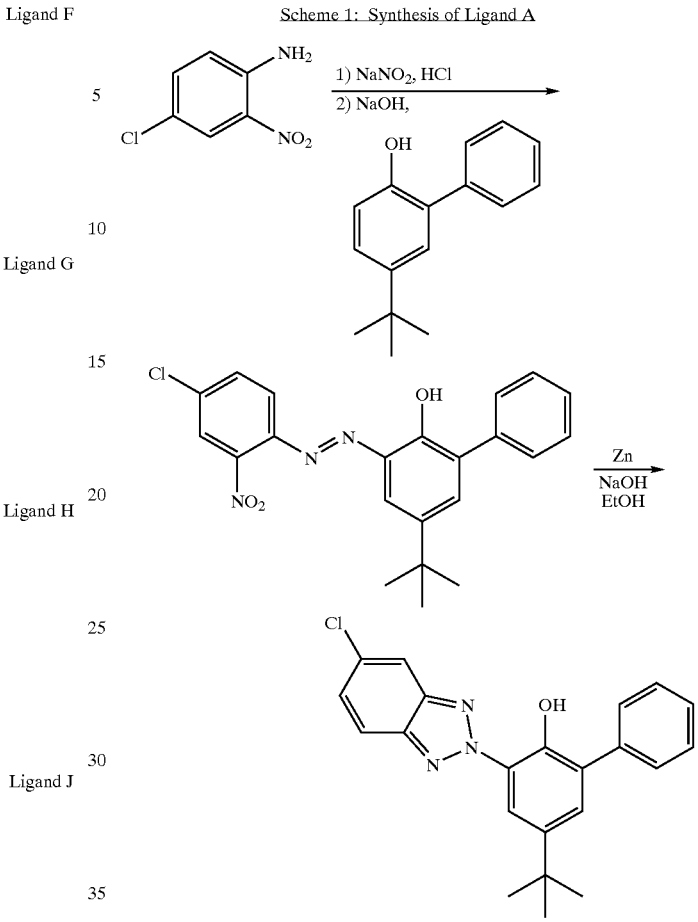

To a suspension of 4-chloro-2-nitroaniline (269 mg, 1.6 mmol) in HCl (37%, 4 mL) is added H$_2$O (1 mL) and NaNO$_2$ (720 μL of a 2.5 M solution in H$_2$O, 1.6 mmol) at 0° C. After stirring at room temperature for 10 minutes the resulting solution is added drop-wise to a solution of 4-tert-butyl-2-phenylphenol (362 mg, 1.16 mmol) and NaOH (2 g, 50 mmol) in H$_2$O (10 mL) and MeOH (10 mL) at 0° C. A precipitate forms which, after the addition is complete, is filtered, dissolved in ethyl acetate, washed with H$_2$O and brine, and dried over Na$_2$SO$_4$. After removal of the solvent, the solid is suspended in a mixture of EtOH (10 mL) and aqueous NaOH (7 mL of a 2 M solution in H$_2$O, 14 mmol). Zn (700 mg, 10.8 mmol) is added and the resulting mixture is stirred for 30 min at 90° C. After filtration, a solution of NH$_4$Cl in H$_2$O is added, the mixture is extracted with ethyl acetate, and the combined organic layers are washed with brine and dried over Na$_2$SO$_4$. Purification by column chromatography over silica gel using hexanes/methylene chloride (10/1) as eluant gives 145 mg (0.385 mmol, 24%) of the desired product as a yellow solid. $^1$H NMR (CDCl$_3$, 400 MHz): δ 11.38 (s, 1H), 8.39 (d, J=2.5 Hz, 1H), 7.92 (d, J=1.5 Hz, 1H), 7.87 (d, J=7 Hz, 1H), 7.64 (dd, J=1.5 Hz/7 Hz, 2H), 7.50–7.35 (m, 5H), 1.41 (s, 9H). One peak in GC-MS, m/z 377.

Ligands B, C, D, E, H and J were prepared following the synthetic methodology used for Ligand A. Ligand F was purchased from Aldrich (CAS registry # 3864-99-1), and Ligand G were purchased from Lancaster (CAS registry # 3864-71-7).

Synthesis of Phenols with Aryl Substitution at the 2-Position:

Ligand Precursor 1:

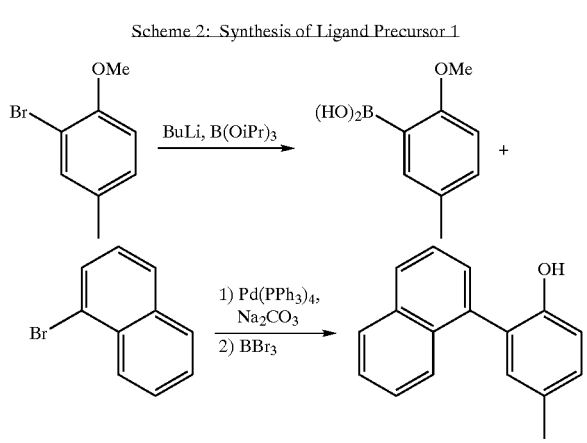

Following Scheme 2, to a solution on 2-bromo-4-methylanisole (10 g, 49.7 mmol) in anhydrous THF (50 mL) is added n-butyllithium (32.6 mL of a 1.6 M solution in hexanes, 52.2 mmol) at −78° C. After stirring at −78° C. for 10 minutes and at room temperature for 1 hour, the solution is cooled again to −78° C. and triisopropyl borate (12.6 mL, 52.2 mmol) is added slowly. After the solution is stirred at room temperature for 1 hour, a solution of $NH_4Cl$ in $H_2O$ is added. The mixture is extracted with ether, and the combined organic layers are washed with brine and dried over $Na_2SO_4$. The crude product is recrystallized from ether to give the 5.6 g of the boronic acid (33.7 mmol, 68%) as a white solid.

Under an atmosphere of argon, $Na_2CO_3$ (10 mL of a 2 M solution in $H_2O$, 20 mmol) is added to a solution of the boronic acid (3.73 g, 22.5 mmol), 1-bromonaphthalene (5 g, 20 mmol), and $Pd(PPh_3)_4$ (462 mg, 0.4 mmol) in DME (40 mL). After stirring for 12 hours at 80° C., $H_2O$ is added and the resulting mixture is extracted with ether. The combined organic layers are washed with brine and dried over $Na_2SO_4$. After removal of the solvent, 5 g of the crude product is obtained.

The crude product is then dissolved in anhydrous methylene chloride (30 mL), and to this solution is then added a solution of $BBr_3$ (24 mL of a 1 M solution in methylene chloride, 24 mmol). After the solution is stirred at room temperature for 1 hour, brine is added. The mixture is extracted with methylene chloride, and the combined organic layers are washed with brine and dried over $Na_2SO_4$. Purification by column chromatography over silica gel using hexanes/ethyl acetate (10/1) as eluant gives 3.3 g (14.1 mmol, 71%) of the desired product as a yellow solid. $^1H$ NMR ($CDCl_3$, 400 MHz): δ 7.95 (d, J=8 Hz, 2H), 7.71 (d, J=8 Hz, 1H), 7.62–7.45 (m, 4H), 7.21 (d, J=8 Hz, 1H), 7.11 (s, 1H), 6.98 (d, J=8 Hz, 1H), 2.39 (s, 3H). $^{13}C$ NMR ($CDCl_3$, 100 MHz): δ 150.9, 134.2, 133.9, 131.8, 131.5, 130.0, 129.7, 128.7, 128.4 (2x), 128.1, 126.7, 126.3, 126.0, 125.7, 115.3, 20.5. One peak in GC-MS, m/z 234.

Synthesis of Phenols with Variation in the 2- and 4-Position:

Ligand Precursor 2:

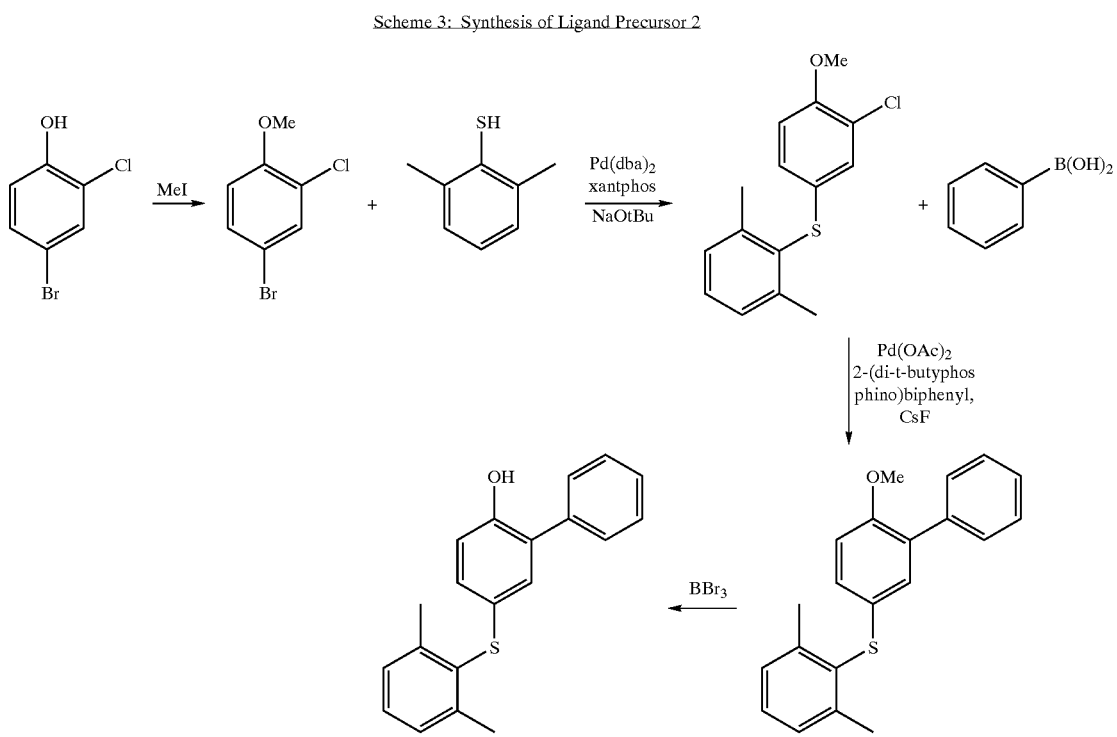

Following Scheme 3, a mixture of 4-bromo-2-chlorophenol (4.66 g, 22.45 mmol), iodomethane (3.1 mL, 50 mmol), and powdered $K_2CO_3$ (13.8 g, 100 mmol) in acetone (20 mL) is stirred at 65° C. for 1 hour. After filtration and removal of the solvent, 4.3 g (19.4 mmol, 86%) of 4-bromo-2-chloroanisole are obtained as a white solid.

The 4-bromo-2-chloroanisole (1 g, 4.52 mmol), plus 2,6-dimethylbenzenethiol (640 μL, 4.8 mmol) and NaOtBu (770 mg, 8 mmol) are then added to a solution of Pd(dba)$_2$ (60 mgs, 0.1 mmol) and xantphos (120 mg, 0.2 mmol) in toluene (10 mL). After stirring the resulting mixture at 110° C. for 3 h, a solution of NH$_4$Cl in H$_2$O is added, the mixture is extracted with hexanes, and the combined organic layers are washed with brine and dried over Na$_2$SO$_4$. Purification by column chromatography over silica gel using hexanes/ethyl acetate (10/1) as eluant gives 1.15 g (4.14 mmol, 92%) of the desired anisole thioether as a yellow oil.

To a solution of Pd(OAc)$_2$ (11 mg, 0.05 mmol) and 2-(di-t-butylphosphino)biphenyl (30 mg, 0.1 mmol) in THF (3 mL) is added the anisole thioether (278 mg, 1 mmol), benzene boronic acid (183 mg, 1.5 mmol) and CsF (456 mgs, 3 mmol). The resulting mixture is stirred at room temperature for 16 h, at 60° C. for 4 hours, and then filtered. Purification by column chromatography over silica gel using hexanes/ethyl acetate (20/1) as eluant gives 293 mg (0.92 mmol, 92%) of the desired 2-phenyl-substituted anisole thioether as a yellow solid (the crude product).

To a solution of the crude product in anhydrous methylene chloride (5 mL) is added BBr$_3$ (1.5 mL of a 1 M solution in methylene chloride, 1.5 mmol). After the solution is stirred at room temperature for 30 minutes, brine is added. The mixture is extracted with methylene chloride, and the combined organic layers are washed with brine and dried over Na$_2$SO$_4$. Purification by column chromatography over silica gel using hexanes/ethyl acetate (20/1) as eluant gives 143 mg (0.47 mmol, 47%) of the desired product as a yellow solid. $^1$H NMR (CDCl$_3$, 400 MHz): δ 7.53–7.37 (3, 6H), 7.25–7.12 (m, 2H), 6.97 (dd, J=1.3 Hz/1.3 Hz, 1H), 6.83 (dd, J=1.3 Hz/1.3 Hz, 2H), 5.12 (s, 1H), 2.48 (s, 6H). One peak in GC-MS, m/z 306.

Example 2

Synthesis of Metal-Ligand Complexes

The following complexes are prepared herein (Bz=benzyl=CH$_2$Ph):

Complex 1

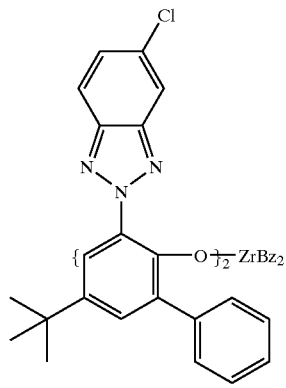

Complex 2

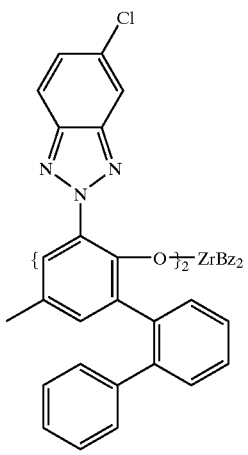

Complex 3

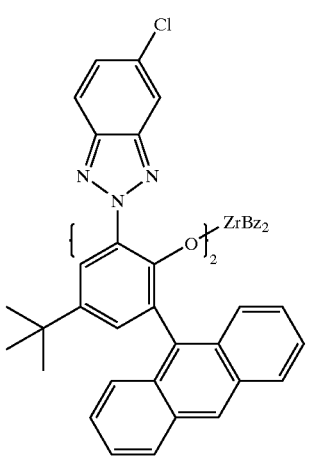

Complex 4

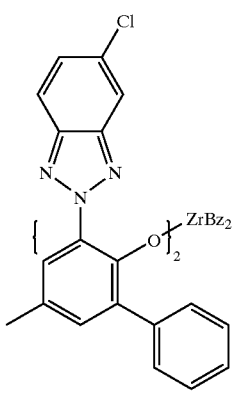

Complex 5

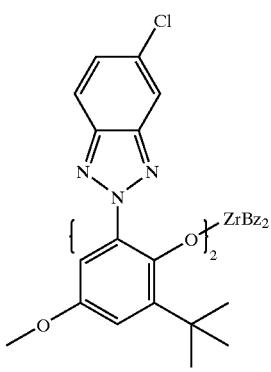

Complex 6

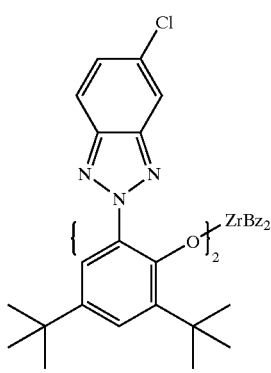

Complex 1. Ligand A (630 mg, 1.67 mmol) was dissolved in $C_6D_6$ (3 mL). Solid $Zr(CH_2Ph)_4$ (380 mg, 0.84 mmol) was added and the mixture was heated to 60° C. for 1 hour. The solvent was removed, and the resulting red-orange solid was extracted into boiling pentane (15 mL) and filtered. The volume of the filtrate was reduced to 5 mL and the filtrate was cooled to −35° C. overnight. An orange precipitate was collected, washed with cold pentane and dried in vacuo (565 mg, 65% yield). $^1$H NMR ($C_6D_6$, 25 C.): δ 8.50 (s, 2H, OAr), 7.94 (d,4H, benzotriazole Ar), 7.69 (s, 2H, OAr or benzoltriazole Ar), 7.45 (s, 2H, OAr or benzoltriazole Ar), 7.1–7.5 (overlapping m, 10H, $CH_2Ph$), 6.2–6.7 (m, 10H, Ph), 2.4 (dd, $Zr(CH_2Ph)$), 1.28 (s, 18H, tBu).

Complex 2: In a manner similar to that described for Complex 1, Complex 2 was prepared from ligand B (77 mg, 0.19 mmol) and $Zr(CH_2Ph)_4$ (46 mg, 0.10 mmol). $^1$H NMR data was consistent with the proposed formula.

Complex 3: In a manner similar to that described for Complex 1, Complex 3 was prepared from ligand C (88 mg, 0.20 mmol) and $Zr(CH_2Ph)_4$ (46 mg, 0.10 mmol). $^1$H NMR data was consistent with the proposed formula.

Complex 4: In a manner similar to that described for Complex 1, Complex 4 was prepared from ligand D (71 mg, 0.21 mmol) and $Zr(CH_2Ph)_4$ (48 mg, 0.11 mmol). $^1$H NMR data was consistent with the proposed formula.

Complex 5: In a manner similar to that described for Complex 1, Complex 5 was prepared from ligand E (75 mg, 0.23 mmol) and $Zr(CH_2Ph)_4$ (58 mg, 0.13 mmol). $^1$H NMR data was consistent with the proposed formula.

Complex 6: In a manner similar to that described for Complex 1, Complex 6 was prepared from ligand F (371 mg, 1.04 mmol) and $Zr(CH_2Ph)_4$ (225 mg, 0.50 mmol). $^1$H NMR data was consistent with the proposed formula.

Examples 3–4

Ethylene-Styrene Copolymerization Experiments

The polymerization reactions were carried out in a parallel pressure reactor (which is described in the patent and patent applications cited above) located within an inert atmosphere drybox. The premixing of the metal-ligand complex or composition with alkyl (group 13 reagent) and activator solutions was performed in an array of 1 mL vials located adjacent to the parallel pressure reactor in the inert atmosphere drybox. A liquid dispensing robot was used to add/remove liquids to/from the 1 mL vials and to inject solutions and liquid reagents into the parallel pressure reactor.

Preparation of the polymerization reactor prior to injection of catalyst composition: A pre-weighed glass vial insert and disposable stirring paddle were fitted to each reaction vessel of the reactor. The reactor was then closed, 0.10 mL of a 0.02 M solution in toluene of the same group 13 reagent used as the "premix alkyl" for each example, followed by 3.8 mL of toluene, were injected into each pressure reaction vessel through a valve. The temperature was then set to 110° C., and the stirring speed was set to 800 rpm, and the mixture was exposed to ethylene at 100 psi pressure. A ethylene pressure of 100 psi in the pressure cell and the temperature setting were maintained, using computer control, until the end of the polymerization experiment.

Preparation of the premix alkyl and activator stock solutions: The activator solution is a 2.5 mM solution of $[PhNMe_2H]^+[B(C_6F_5)_4]^-$ (N,N'-dimethylanilinium tetrakis (pentafluorophenyl) borate, "ABF20") in toluene heated to approximately 85° C. to dissolve the reagent, or a 2.5 mM toluene solution of $[PhN((CH_2)_{n''}CH_3)_2H]^+$ $[B(C_6F_5)_4]^-$ (where n" is 14, 16 or 18, shown in table 2a as $[PhNR_2H]^+$ $[B(C_6F_5)_4]^-$) or a 7.5 mM toluene solution of $B(C_6F_5)_3$. The premix alkyl ("group 13 reagent") solution is either a 0.050 M solution of Akzo-Nobel polymethylaluminoxane-improved process (PMAO-IP) or a 0.050 M solution of Akzo-Nobel modified methylaluminoxane-3A (MMAO), or a 0.20 M solution of diisobutyl aluminum hydride (DIBAL-H). All "group 13 reagent" solutions were solutions in toluene. See also WO 02/02577 for activator synthesis for examples 3.7, 3.8, 3.9 and 3.11.

Polymerization: After injection of solutions into the pressure reactor vessel (described below) the polymerization reactions were allowed to continue at 110° C. polymerization temperature for the time shown in tables 1b, 2b, 3b and 4b (shown for each example as "Run time"), during which time the temperature and pressure were maintained at their pre-set levels by computer control. The polymerization times were the lesser of the maximum desired polymerization reaction time or the time taken for a predetermined amount of ethylene gas to be consumed in the polymerization reaction. After the reaction time elapsed, the reaction was quenched by addition of an overpressure of carbon dioxide sent to the reactor.

Product work-up: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly in a vacuum oven at 75° C. The vial was then weighed to determine the yield of polymer product. The polymer product was then analyzed by rapid GPC, as described above to determine the molecular weight of the polymer produced, and by FTIR spectroscopy to determine the styrene content. Selected samples were additionally analyzed using $^1$H NMR spectroscopy for styrene incorporation and vinyl end group content.

Example 3

Ethylene-Styrene Copolymerization Using Metal-Ligand Complexes 12 polymerization reactions were carried out with different metal-ligand complexes for the copolymerization of ethylene and styrene. For the following descriptions, the volumes of the reagent solutions added to the 1 mL vial and to the pre-pressurized polymerization reaction vessel are shown in tables 1a and 2a. Polymerization results and product data are shown in tables 1b and 2b.

Injection of solutions into the pressure reactor vessel (after "preparation of the polymerization reactor" and immediately prior to "polymerization") for Example 3.1–3.12.: First, the appropriate amount ("premix alkyl volume") of the 0.050 M group 13 reagent solution (e.g. 0.040 mL of 0.050 M solution of PMAO-IP for Example 3.1) was dispensed into a 1 mL vial. Then the appropriate amount of the toluene solution of the metal-ligand complex ("complex volume") was added to the 1 mL vial (e.g. 0.080 mL of a 5 mM solution (0.40 $\mu$mol) of Complex 1 for Example 3.1). This mixture was held at room temperature for 1 minute, during which time 0.420 mL of styrene followed immediately by 0.380 mL of toluene were injected into the pre-pressurized reaction vessel. Then, an appropriate amount ("activator volume") of the activator solution (e.g. 0. 176 mL of a 2.5 mM toluene solution (0.44 $\mu$mol) of N,N'-dimethylanilinium tetrakis (pentafluorophenyl) borate ("ABF20") for Example 3.1) was added to the 1 mL vial. For Example 3.6, 0.40 mL of toluene was added to the 1 mL vial prior to addition of the other reagents, bringing the total volume of the 1 mL via contents to 0.724 mL after addition of the premix alkyl, complex and activator solutions. For Example 3.12, 0.185 mL of toluene was added to the 1 mL vial prior to addition of the other reagents, bringing the total volume of the 1 mL via contents to 0.370 mL after addition of the premix alkyl, complex and activator solutions. After 30 seconds, an appropriate volume (the "injection volume", calculated as the total volume of the 1 mL vial contents multiplied by the "injection fraction") was aspirated from the 1 mL vial and injected into the pre-pressurized reaction vessel (e.g. for Example 3.1 this corresponds to a total volume of 0.296 mL multiplied an "injection fraction" of 0.25, providing an injection volume of 0.074 mL, corresponding 0.10 $\mu$mol of the complex), followed immediately by approximately 0.7 mL of toluene injected into the pre-pressurized polymerization reaction vessel, to bring the total solution volume in the pressurized reaction vessel to 5.5 mL. The polymerization and product work-up were then performed as described above.

Example 4

Preparation of Ligand/Metal Compositions and Ethylene/Styrene Co-Polymerizations Using Ligand/Metal Compositions For the following descriptions, the volumes of the reagent solutions added to the 1 mL vial and to the pre-pressurized polymerization reaction vessel are shown in tables 3a and 4a. Polymerization results and product data are shown in tables 3b and 4b.

In situ preparation of metal-ligand compositions: Stock solutions were prepared as follows: The "metal precursor solution" is a 10 mM solution of $Zr(CH_2Ph)_4$ or $Hf(CH_2Ph)_4$ or $Zr(NMe_2)_4$ or $Hf(NMe_2)_4$ in toluene. The "ligand solutions" are 25 mM solutions of the representative ligands in toluene, (0.80 $\mu$mol), prepared in an array of 1 mL glass vials by dispensing 0.032 mL of a 25 mM ligand solution (0.80 $\mu$mol) in a 1 mL glass vial. To each 1 mL glass vial containing ligand/toluene solution was added 0.040 mL of the metal precursor solution (0.40 $\mu$mol), to form the metal-ligand combination solution.

For Examples 4.1–4.4 and 4.6–4.9 the reaction mixtures we heated to 70° C. for 1 hour, after which time the products were cooled to ambient temperature. Prior to addition of alkylation and activator solution, the volume of the metal-ligand combination solution (which was reduced due to solvent evaporation) was measured, and this "initial solvent volume" was used in subsequent calculations of vial contents total volume and the "injection volume". For Examples 4.3 and 4.4 an additional 0. 10 mL of toluene was added to the 1 mL vial at this stage.

For Examples 4.5 and 4.10 the reaction mixtures were heated to 80° C. for 1.5 hours, after which time the products were cooled to ambient temperature. The reaction mixtures were then dried completely by blowing a stream of argon over the 1 ml vial. Prior to addition of the premix alkyl (group 13 reagent) solution and activator solution, a volume of toluene (shown in table 3a as "initial solvent volume") was added to 1 mL vial containing the metal-ligand combination solution. This "initial solvent volume" was used in subsequent calculations of vial contents total volume and the "injection volume".

Injection of solutions into the pressure reactor vessel (after "preparation of the polymerization reactor" and immediately prior to "polymerization") for Examples 4.1–4.10: To the ligand-metal composition, a volume (shown in table 3a or 4a for each example) of a 500 mM solution of 1-octene in toluene was added. Then, an appropriate amount of the group 13-reagent solution (shown in table 3a or 4a for each example) was added to the 1 mL vial. This mixture was held at room temperature either for 1 minute for Examples 4.1–4.4 and 4.6–4.9, or for 10 minutes for Examples 4.5 and 4.10, during which time 0.420 mL of styrene followed immediately by 0.380 mL of toluene, were injected into the pre-pressurized reaction vessel. Then, an appropriate amount of the "activator solution" (shown in table 3a or 4a for each example) was added to the 1 mL vial. After a wait time of 30 seconds, a fraction (the "injection fraction" shown in table 3a or 4a) of the total volume of the 1 mL vial contents (the "injection volume") was injected into the pre-pressurized reaction vessel, followed immediately by approximately 0.7 mL of toluene, to bring the total solution volume in the pressurized reaction vessel to 5.5 mL. The polymerization and product work-up were then performed as described above.

TABLE 1a

Ethylene-Styrene Copolymerization Experiments using isolated complexes: Solution Premix and Injection Details

| | \multicolumn{6}{c}{Example #} |
|---|---|---|---|---|---|---|
| | 3.1 | 3.2 | 3.3 | 3.4 | 3.5 | 3.6 |
| Complex # | 1 | 3 | 3 | 2 | 2 | 6 |
| Complex solution concentration (M) | 0.005 | 0.005 | 0.005 | 0.005 | 0.005 | 0.004 |
| Complex Volume (mL) | 0.080 | 0.080 | 0.080 | 0.080 | 0.080 | 0.100 |
| $\mu$mol of complex added to 1 mL vial | 0.40 | 0.40 | 0.40 | 0.40 | 0.40 | 0.40 |
| Premix Alkyl (group 13 reagent) | PMAO-IP | PMAO-IP | PMAO-IP | PMAO-IP | MMAO | PMAO-IP |
| Premix Alkyl Volume (mL) | 0.040 | 0.040 | 0.040 | 0.040 | 0.040 | 0.048 |
| Premix Alkyl/Zr ratio | 5/1 | 5/1 | 5/1 | 5/1 | 5/1 | 6/1 |
| Activator | ABF20 | ABF20 | ABF20 | ABF20 | ABF20 | ABF20 |
| Activator Volume (mL) | 0.176 | 0.176 | 0.176 | 0.176 | 0.176 | 0.176 |
| Activator/Zr ratio | 1.1/1 | 1.1/1 | 1.1/1 | 1.1/1 | 1.1/1 | 1.1/1 |
| Injection Fraction | 0.25 | 0.25 | 0.125 | 0.125 | 0.125 | 0.0075 |
| Injection Volume (mL) | 0.074 | 0.074 | 0.037 | 0.037 | 0.037 | 0.005 |
| $\mu$mol Zr injected into reactor | 0.10 | 0.10 | 0.05 | 0.05 | 0.05 | 0.003 |

TABLE 1b

Ethylene-Styrene Copolymerization Experiments using isolated complexes: Polymerization Details and Results

| | \multicolumn{6}{c}{Example #} |
|---|---|---|---|---|---|---|
| | 3.1 | 3.2 | 3.3 | 3.4 | 3.5 | 3.6 |
| Complex # | 1 | 3 | 3 | 2 | 2 | 6 |
| $\mu$mol Zr injected into reactor | 0.10 | 0.10 | 0.05 | 0.05 | 0.05 | 0.003 |
| Run Time (Minutes) | 10.7 | 3.1 | 5.5 | 9.2 | 4.1 | 10.0 |
| Polymer Yield (mg) | 202 | 148 | 124 | 140 | 166 | 82 |
| Activity (mg polymer per $\mu$mol per minute) | 188 | 479 | 454 | 305 | 815 | 2717 |
| mol % incorporated Styrene by $^1$H NMR | 11.1 | 10.0 | 9.4 | 9.8 | 11.1 | 4.9 |
| Average # Styrene units per chain (by $^1$H NMR) | 2.5 | 1.3 | 1.2 | 1.3 | 1.5 | 1.3 |
| Average # Ethylene units per chain (by $^1$H NMR) | 20 | 12 | 12 | 12 | 12 | 25 |
| Average # monomer units per chain (by $^1$H NMR) | 22 | 13 | 13 | 13 | 13 | 27 |
| Mn by $^1$H NMR | 810 | 460 | 450 | 460 | 480 | 840 |
| Ratio of methyl/vinyl region integrations ($^1$H NMR) | 1.0 | 0.9 | 0.8 | 0.9 | 0.9 | 1.1 |
| mol % total styrene by FTIR (linear regression) | 12.9 | 12.3 | 11.2 | 12.3 | 13.1 | 6.2 |
| Mw × 10$^{-3}$ (by GPC) | 3.4 | 2.4 | 2.5 | 3.0 | 3.0 | 2.2 |
| Mw/Mn (by GPC) | 1.5 | 1.4 | 1.4 | 1.4 | 1.5 | 1.3 |

TABLE 2a

Ethylene-Styrene Copolymerization Experiments using isolated complexes: Solution Premix and Injection Details

| | Example # | | | | | |
|---|---|---|---|---|---|---|
| | 3.7 | 3.8 | 3.9 | 3.10 | 3.11 | 3.12 |
| Complex # | 1 | 3 | 2 | 1 | 4 | 5 |
| Complex solution concentration (M) | 0.005 | 0.005 | 0.005 | 0.005 | 0.005 | 0.004 |
| Complex Volume (mL) | 0.080 | 0.080 | 0.080 | 0.050 | 0.050 | 0.050 |
| μmol of complex added to 1 mL vial | 0.40 | 0.40 | 0.40 | 0.25 | 0.25 | 0.20 |
| Premix Alkyl (group 13 reagent) | PMAO-IP | PMAO-IP | MMAO | MMAO | MMAO | MMAO |
| Premix Alkyl Volume (mL) | 0.040 | 0.040 | 0.040 | 0.025 | 0.025 | 0.025 |
| Premix Alkyl/Zr ratio | 5/1 | 5/1 | 5/1 | 5/1 | 5/1 | 5/1 |
| Activator | $[PhNR_2H]^+$ $[B(C_6F_5)_4]^-$ | $[PhNR_2H]^+$ $[B(C_6F_5)_4]^-$ | $[PhNR_2H]^+$ $[B(C_6F_5)_4]^-$ | $B(C_6F_5)_3$ | $[PhNR_2H]^+$ $[B(C_6F_5)_4]^-$ | $B(C_6F_5)_3$ |
| Activator Volume (mL) | 0.176 | 0.176 | 0.176 | 0.110 | 0.110 | 0.110 |
| Activator/Zr ratio | 1.1/1 | 1.1/1 | 1.1/1 | 3.3/1 | 1.1/1 | 3.3/1 |
| Injection Fraction | 0.125 | 0.125 | 0.125 | 0.40 | 0.40 | 0.063 |
| Injection Volume (mL) | 0.037 | 0.037 | 0.037 | 0.074 | 0.074 | 0.023 |
| μmol Zr injected into reactor | 0.050 | 0.050 | 0.050 | 0.10 | 0.10 | 0.013 |

TABLE 2b

Ethylene-Styrene Copolymerization Experiments using isolated complexes.

| | Example # | | | | | |
|---|---|---|---|---|---|---|
| | 3.7 | 3.8 | 3.9 | 3.10 | 3.11 | 3.12 |
| Complex # | 1 | 3 | 2 | 1 | 4 | 5 |
| μmol Zr injected into reactor | 0.050 | 0.050 | 0.050 | 0.10 | 0.10 | 0.013 |
| Run Time (Minutes) | 5.6 | 6.1 | 2.7 | 5.0 | 3.9 | 5.7 |
| Polymer Yield (mg) | 225 | 122 | 193 | 219 | 232 | 154 |
| Activity (mg polymer per μmol Zr per minute) | 797 | 396 | 1428 | 438 | 589 | 2140 |
| Mol % total styrene by FTIR (linear regression) | 14.0 | 11.4 | 14.0 | 13.4 | 14.8 | 4.8 |
| Mw × $10^{-3}$ (by GPC) | 3.5 | 2.5 | 3.0 | 2.7 | 2.5 | 3.0 |
| Mw/Mn (by GPC) | 1.4 | 1.2 | 1.3 | 1.2 | 1.2 | 1.2 |

TABLE 3a

In-situ preparation of zirconium metal-ligand compositions and solution premix and injection details.

| | Example # | | | | |
|---|---|---|---|---|---|
| | 4.1 | 4.2 | 4.3 | 4.4 | 4.5 |
| Metal Precursor | $Zr(CH_2Ph)_4$ | $Zr(CH_2Ph)_4$ | $Zr(CH_2Ph)_4$ | $Zr(CH_2Ph)_4$ | $Zr(NMe_2)_4$ |
| Ligand | Ligand D | Ligand C | Ligand E | Ligand G | Ligand C |

TABLE 3a-continued

In-situ preparation of zirconium metal-ligand compositions and solution premix and injection details.

| | Example # | | | | |
|---|---|---|---|---|---|
| | 4.1 | 4.2 | 4.3 | 4.4 | 4.5 |
| Metal Precursor Solution concentration (M) | 0.010 | 0.010 | 0.010 | 0.010 | 0.010 |
| Metal Precursor Volume (mL) | 0.040 | 0.040 | 0.040 | 0.040 | 0.040 |
| μmol of metal added to 1 mL vial | 0.40 | 0.40 | 0.40 | 0.40 | 0.40 |
| Ligand Solution concentration (M) | 0.025 | 0.025 | 0.025 | 0.025 | 0.025 |
| Ligand Solution Volume (mL) | 0.032 | 0.032 | 0.032 | 0.032 | 0.032 |
| μmol of Ligand added to 1 mL vial | 0.080 | 0.080 | 0.080 | 0.080 | 0.080 |
| Complexation Time | 1 hour | 1 hour | 1 hour | 1 hour | 1.5 hours |
| Complexation Temperature | 70° C. | 70° C. | 70° C. | 70° C. | 80° C. |
| Solvent volume lost to evaporation | 0.030 | 0.030 | 0.030 | 0.030 | 0.080 |
| Volume of Solvent Added to vial (mL) | 0 | 0 | 0.100 | 0.100 | 0.070 |
| Initial Solvent Volume (mL) | 0.050 | 0.050 | 0.150 | 0.150 | 0.070 |
| Volume of 0.5 M 1-octene solution added to vial (mL) | 0.024 | 0.024 | 0.024 | 0.024 | 0.024 |
| Premix Alkyl (group 13 reagent) | MMAO | MMAO | MMAO | PMAO-IP | DIBAL-H |
| Premix Alkyl concentration (M) | 0.050 | 0.050 | 0.050 | 0.050 | 0.20 |
| Premix Alkyl Volume (mL) | 0.048 | 0.048 | 0.048 | 0.048 | 0.060 |
| Premix Alkyl/Zr ratio | 6/1 | 6/1 | 6/1 | 6/1 | 30/1 |
| Activator (2.5 mM) | ABF20 | ABF20 | ABF20 | ABF20 | ABF20 |
| Activator Volume (mL) | 0.176 | 0.176 | 0.176 | 0.176 | 0.176 |
| Activator/Zr ratio | 1.1/1 | 1.1/1 | 1.1/1 | 1.1/1 | 1.1/1 |
| Injection Fraction | 0.050 | 0.050 | 0.025 | 0.025 | 0.25 |
| Injection Volume (mL) | 0.015 | 0.015 | 0.010 | 0.010 | 0.083 |
| μmol Zr injected into reactor | 0.020 | 0.020 | 0.010 | 0.010 | 0.10 |

TABLE 3b

Results of ethylene-styrene copolymerizations employing zirconium metal-ligand compositions.

| | Example # | | | | |
|---|---|---|---|---|---|
| | 4.1 | 4.2 | 4.3 | 4.4 | 4.5 |
| Metal Precursor | $Zr(CH_2Ph)_4$ | $Zr(CH_2Ph)_4$ | $Zr(CH_2Ph)_4$ | $Zr(CH_2Ph)_4$ | $Zr(NMe_2)_4$ |
| Ligand | Ligand D | Ligand C | Ligand E | Ligand G | Ligand C |
| μmol Zr injected into reactor | 0.020 | 0.020 | 0.010 | 0.010 | 0.10 |
| Run Time (Minutes) | 15.0 | 3.6 | 2.3 | 1.5 | 3.1 |
| Polymer Yield (mg) | 105 | 128 | 211 | 141 | 108 |
| Activity (mg polymer per μmol Zr per minute) | 348 | 1801 | 9183 | 9200 | 347 |
| mol % incorporated Styrene by $^1$H NMR | 10.3 | 10.1 | — | — | — |

TABLE 3b-continued

Results of ethylene-styrene copolymerizations employing zirconium metal-ligand compositions.

| | Example # | | | | |
|---|---|---|---|---|---|
| | 4.1 | 4.2 | 4.3 | 4.4 | 4.5 |
| mol % total styrene by FTIR (linear regression) | 12.1 | 12.8 | 8.2 | 6.6 | 13.7 |
| Mw × $10^{-3}$ (by GPC) | 3.2 | 2.4 | 3.6 | 2.6 | 2.3 |
| Mw/Mn (by GPC) | 1.2 | 1.2 | 1.3 | 1.2 | 1.3 |

TABLE 4a

In-situ preparation of hafnium metal-ligand compositions and solution premix and injection details.

| | Example # | | | | |
|---|---|---|---|---|---|
| | 4.6 | 4.7 | 4.8 | 4.9 | 4.10 |
| Metal Precursor | $Hf(CH_2Ph)_4$ | $Hf(CH_2Ph)_4$ | $Hf(CH_2Ph)_4$ | $Hf(CH_2Ph)_4$ | $Hf(NMe_2)_4$ |
| Ligand | Ligand D | Ligand C | Ligand E | Ligand G | Ligand C |
| Metal Precursor Solution concentration (M) | 0.010 | 0.010 | 0.010 | 0.010 | 0.010 |
| Metal Precursor Volume (mL) | 0.040 | 0.040 | 0.040 | 0.040 | 0.040 |
| µmol of metal added to 1 mL vial | 0.40 | 0.40 | 0.40 | 0.40 | 0.40 |
| Ligand Solution concentration (M) | 0.025 | 0.025 | 0.025 | 0.025 | 0.025 |
| Ligand Solution Volume (mL) | 0.032 | 0.032 | 0.032 | 0.032 | 0.032 |
| µmol of Ligand added to 1 mL vial | 0.080 | 0.080 | 0.080 | 0.080 | 0.080 |
| Complexation Time | 1 hour | 1 hour | 1 hour | 1 hour | 1.5 hours |
| Complexation Temperature | 70° C. | 70° C. | 70° C. | 70° C. | 80° C. |
| Solvent volume lost to evaporation | 0.030 | 0.030 | 0.030 | 0.030 | 0.080 |
| Volume of Solvent Added to vial (mL) | 0 | 0 | 0 | 0 | 0.070 |
| Initial Solvent Volume (mL) | 0.050 | 0.050 | 0.050 | 0.050 | 0.070 |
| Volume of 0.5 M 1-octene solution added to vial (mL) | 0.024 | 0.024 | 0.024 | 0.024 | 0.024 |
| Premix Alkyl (group 13 reagent) | MMAO | MMAO | MMAO | PMAO-IP | DIBAL-H |
| Premix Alkyl concentration (M) | 0.050 | 0.050 | 0.050 | 0.050 | 0.20 |
| Premix Alkyl Volume (mL) | 0.048 | 0.048 | 0.048 | 0.048 | 0.060 |
| Premix Alkyl/Zr ratio | 6/1 | 6/1 | 6/1 | 6/1 | 30/1 |
| Activator (2.5 mM) | ABF20 | ABF20 | ABF20 | ABF20 | ABF20 |
| Activator Volume (mL) | 0.176 | 0.176 | 0.176 | 0.176 | 0.176 |
| Activator/Zr ratio | 1.1/1 | 1.1/1 | 1.1/1 | 1.1/1 | 1.1/1 |
| Injection Fraction | 0.25 | 0.25 | 0.25 | 0.05 | 0.50 |
| Injection Volume (mL) | 0.075 | 0.075 | 0.075 | 0.015 | 0.165 |
| µmol Zr injected into reactor | 0.10 | 0.10 | 0.10 | 0.020 | 0.20 |

TABLE 4b

Results of ethylene-styrene copolymerizations employing hafnium metal-ligand compositions.

| | Example # | | | | |
|---|---|---|---|---|---|
| | 4.6 | 4.7 | 4.8 | 4.9 | 4.10 |
| Metal Precursor | $Hf(CH_2Ph)_4$ | $Hf(CH_2Ph)_4$ | $Hf(CH_2Ph)_4$ | $Hf(CH_2Ph)_4$ | $Hf(NMe_2)_4$ |
| Ligand | Ligand D | Ligand C | Ligand E | Ligand G | Ligand C |
| μmol Hf injected into reactor | 0.10 | 0.10 | 0.10 | 0.020 | 0.20 |
| Run Time (Minutes) | 15.0 | 15.0 | 3.8 | 15 | 15 |
| Polymer Yield (mg) | 61 | 84 | 194 | 70 | 97 |
| Activity (mg polymer per μmol Hf per minute) | 41 | 56 | 506 | 230 | 32 |
| mol % total styrene by FTIR (linear regression) | 8.2 | 5.0 | 2.6 | 3.4 | 5.6 |
| Mw × $10^{-3}$ by GPC | 6.8 | 3.2 | 8.0 | 5.5 | 2.3 |
| Mw/Mn by GPC | 1.5 | 1.2 | 1.6 | 1.4 | 1.3 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A copolymer of ethylene and styrene having a molecular weight of less than about 10,000, said copolymer having at least one end that is a vinyl group and at least a second end that is a methyl group and wherein the ratio of said methyl to said vinyl is about 0.8:1 to about 1:0.8.

2. The copolymer of claim 1, wherein said molecular weight is less than about 5,000.

3. The copolymer of claim 1, wherein said molecular weight is less than about 3,000.

4. The copolymer of claim 1, wherein said molecular weight is less than about 1,000.

5. The copolymer of claim 1, wherein said molecular weight is a weight average molecular weight.

6. The copolymer of claim 1, wherein said molecular weight is a number average molecular weight.

7. The copolymer of claim 1, wherein said ratio is about 0.9:1 to about 1:0.9.

8. A compound characterized by either of the general formulas:

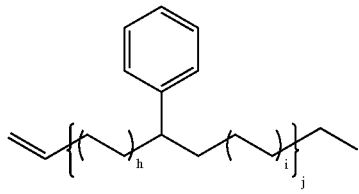

I

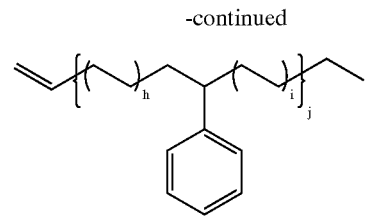

II wherein h, i and j are each a number greater than or equal to 1 and the molecular weight of said compound is less than about 10,000.

9. The compound of claim 8, wherein said molecular weight is less than about 5,000.

10. The compound of claim 8, wherein said molecular weight is less than about 3,000.

11. The compound of claim 8, wherein said molecular weight is less than about 1,000.

12. The compound of claim 8, wherein (h+i+1)*j)+2 in a bulk sample is between 5 and 100.

13. The compound of claim 8, wherein (h+i+1)*j)+2 in a bulk sample is between 5 and 50.

14. The compound of claim 8, wherein (h+i+1)*j)+2 in a bulk sample is between 5 and 25.

15. The compound of claim 8, wherein j is a number between 1 and 10.

16. The compound of claim 8, wherein j is a number between 1 and 5.

17. The compound of claim 8, wherein j is a number between 1 and 3.

18. The compound of claim 8, wherein j is a number between 2 and 10.

19. The compound of claim 8, wherein j is a number between 2 and 5.

20. The compound of claim 8, wherein said compound is a copolymer is produced by polymerization of ethylene and styrene with the aid of a catalyst that comprises Hf, Zr or Ti.

21. The compound of claim 20, wherein said catalyst is formed from a composition comprising a ligand and metal precursor, wherein said ligand is characterized by the following formula:

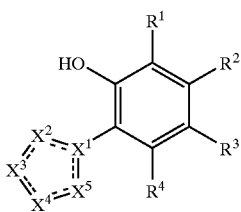

wherein $X^1$ and $X^2$ are N, and $X^3$, $X^4$, and $X^5$ are independently selected from the group consisting of N and $CR^{15}$, where $R^{15}$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof, provided that at least one and not more than two of $X^3$, $X^4$, and $X^5$ are N; optionally, $X^3$ and $X^4$ may be joined to form a fused ring system having up to 50 atoms, not counting hydrogen atoms; and $R^1$, $R^2$, $R^3$ and $R^4$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thio, seleno, nitro, and combinations thereof, with the exception that $R^1$ may not be hydrogen, and optionally two or more of $R^1$, $R^2$, $R^3$ and $R^4$ may be joined to form a fused ring system having up to 50 atoms, not counting hydrogen atoms; and wherein said metal precursor comprises a group 4 metal.

* * * * *